United States Patent [19]
Tabata et al.

[11] Patent Number: 5,434,669
[45] Date of Patent: Jul. 18, 1995

[54] MEASURING INTERFEROMETRIC ENDOSCOPE HAVING A LASER RADIATION SOURCE

[75] Inventors: Seiichiro Tabata; Hiroyuki Kurita; Susumu Takahashi, all of Hachiouji; Katsunori Sakiyama, Akikawa; Toshikazu Takayama, Hachiouji, all of Japan

[73] Assignee: Olympus Optical Co., Ltd., Tokyo, Japan

[21] Appl. No.: 160,258

[22] Filed: Dec. 2, 1993

Related U.S. Application Data

[63] Continuation-in-part of Ser. No. 781,585, Oct. 23, 1991, abandoned.

[30] Foreign Application Priority Data

Oct. 23, 1990 [JP] Japan ................... 2-285652
Jul. 4, 1991 [JP] Japan ................... 3-164656

[51] Int. Cl.⁶ ............................................. G01B 9/02
[52] U.S. Cl. ....................... 356/345; 356/360; 356/241; 600/160
[58] Field of Search ............... 356/345, 351, 359, 360, 356/241; 128/4, 6

[56] References Cited

U.S. PATENT DOCUMENTS

| 4,139,304 | 2/1979 | Redman et al. | 356/358 |
| 4,212,073 | 7/1980 | Balasubramanian | 356/376 |
| 4,643,514 | 2/1987 | Raviv et al. | 356/347 |
| 4,948,251 | 8/1990 | Kondo | 356/351 |

FOREIGN PATENT DOCUMENTS 0069721  4/1984  Japan .

*Primary Examiner*—Samuel A. Turner
*Attorney, Agent, or Firm*—Cushman, Darby & Cushman

[57] ABSTRACT

The measuring endoscope includes a device for producing interference fringes, a device for projecting the interference fringes onto a surface of an object to be measured, a device for scanning the interference fringes, an imaging device for reading vibrations of brightness on the surface of the object to be measured which are caused by the scanning of the interference fringes and a processing device capable of determining depths of concavities and heights of convexities on the surface the measured object by calculating data output from the imaging device. This measuring endoscope makes it possible to determine accurately the location of internal diseases within organs of human bodies, defects in gas pipes and so on.

8 Claims, 16 Drawing Sheets

ENDOSCOPE TIP DISTAL END

ENDOSCOPE TIP DISTAL END

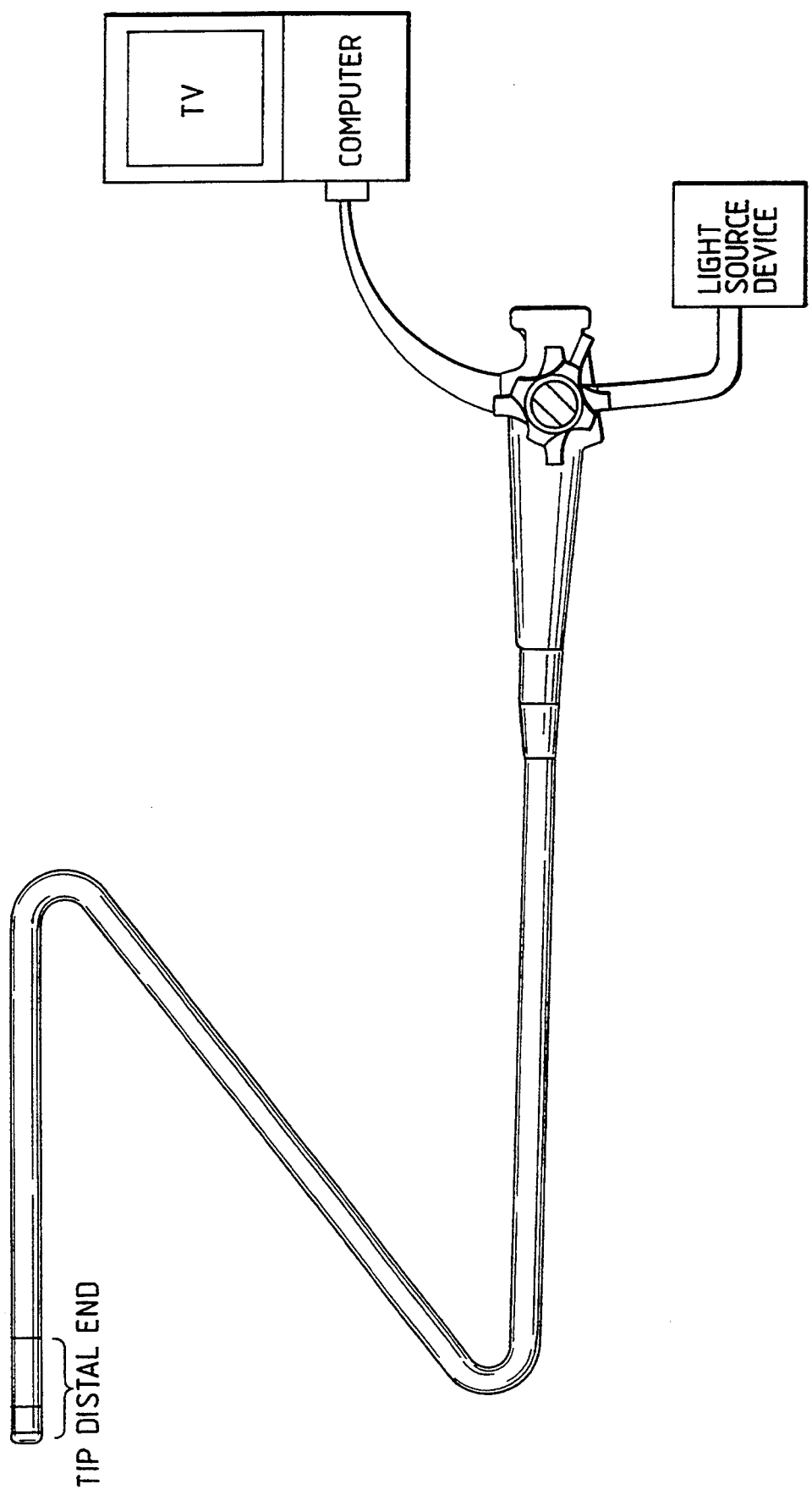

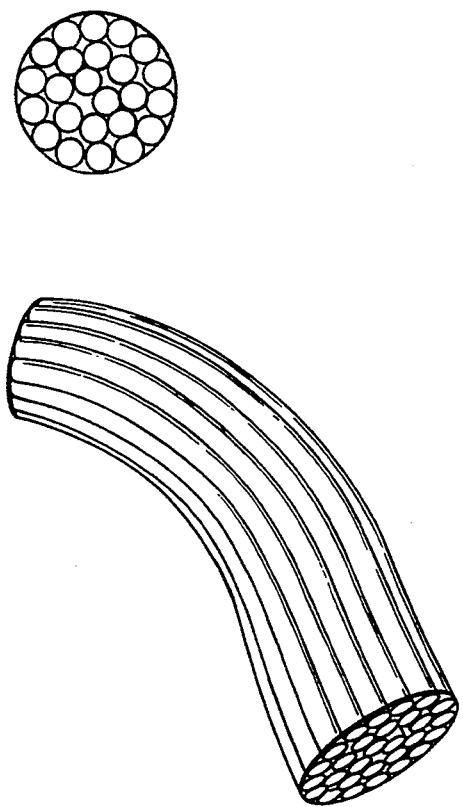
FIG. 7
FIG. 6
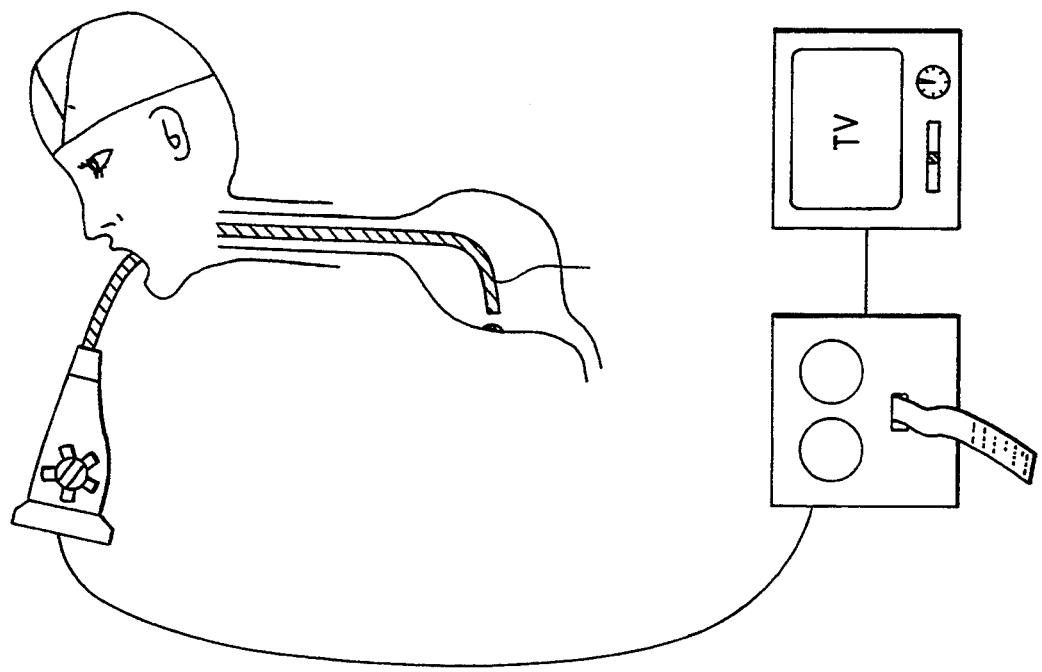
FIG. 5

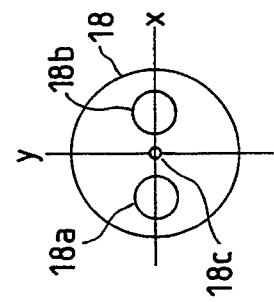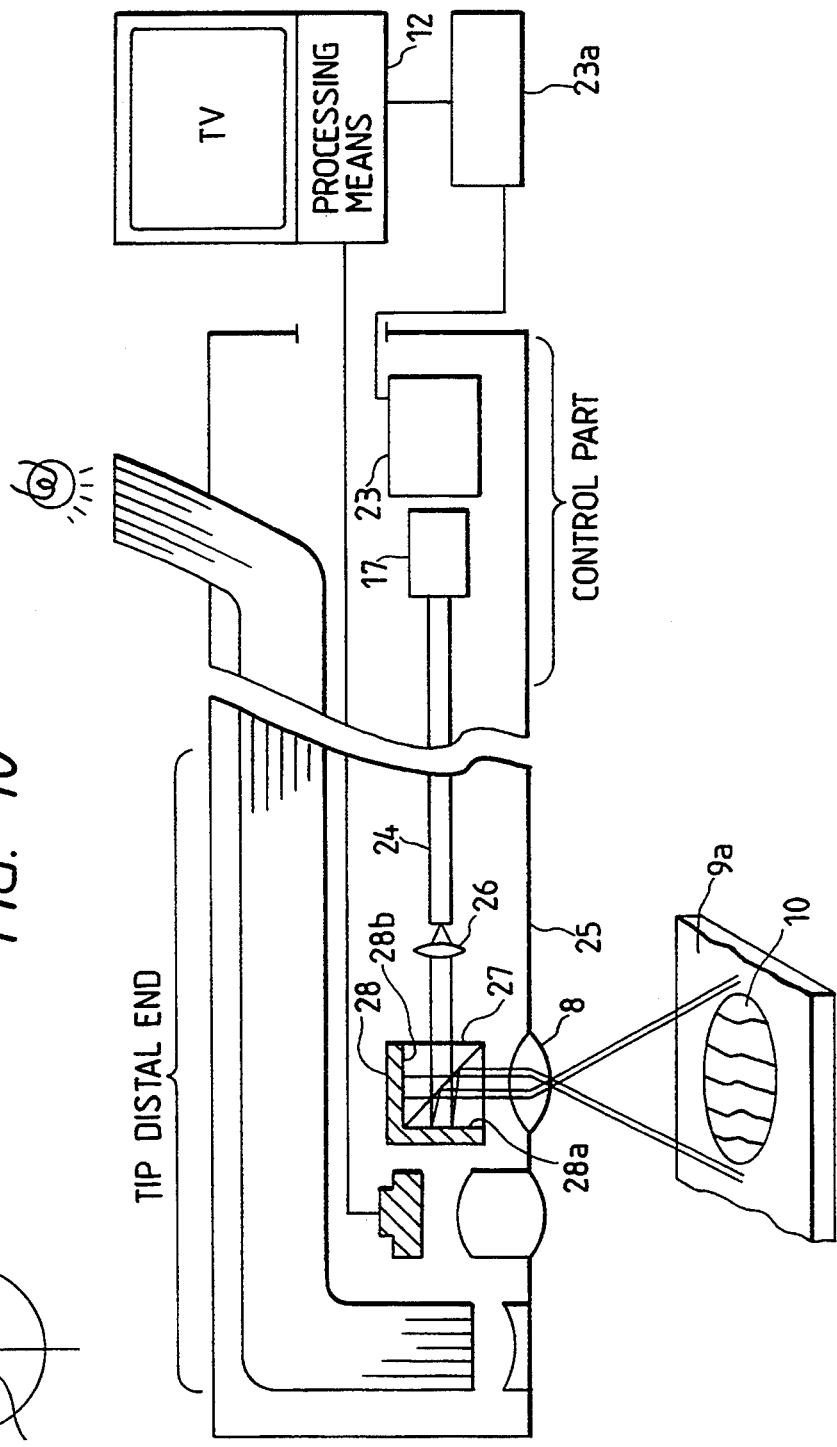
FIG. 9
FIG. 10

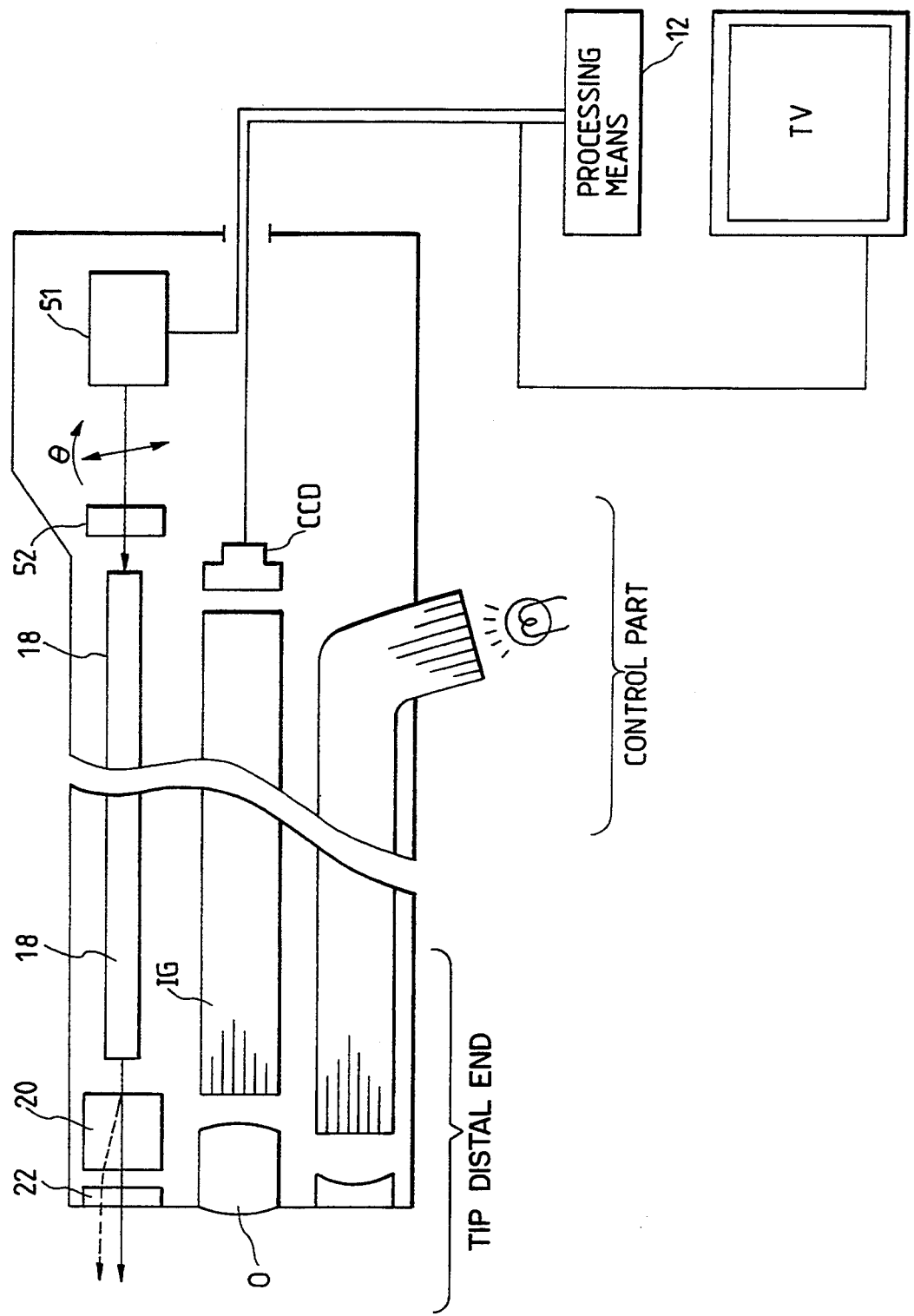

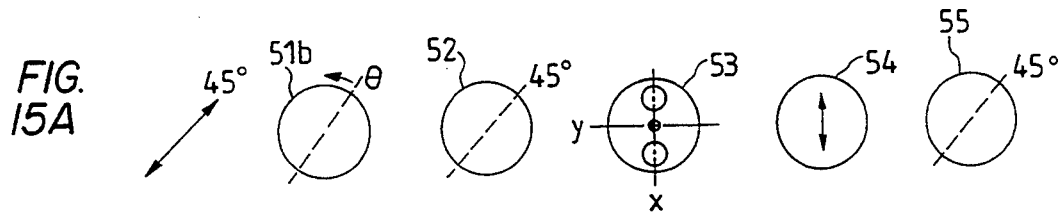
FIG. 15A
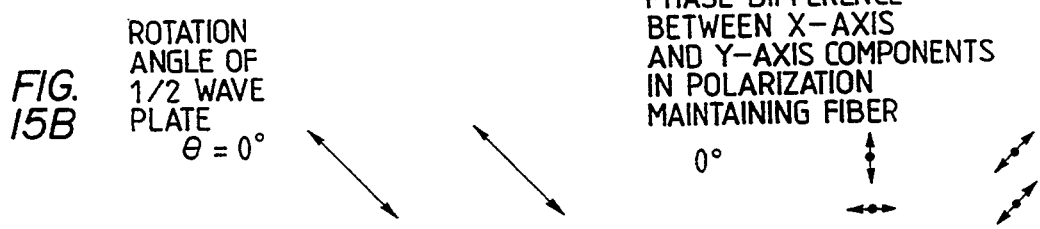
FIG. 15B  ROTATION ANGLE OF 1/2 WAVE PLATE θ = 0°
PHASE DIFFERENCE BETWEEN X-AXIS AND Y-AXIS COMPONENTS IN POLARIZATION MAINTAINING FIBER
0°
FIG. 15C  θ = 22.5°  90°
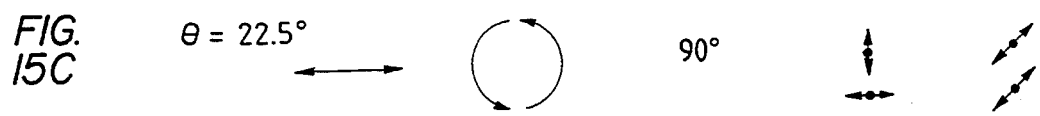
FIG. 15D  θ = 45°  180°
FIG. 15E  θ = 67.5°  270°
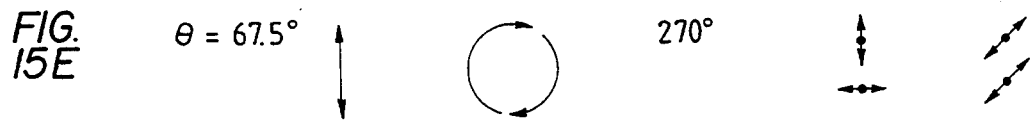

MEASURING INTERFEROMETRIC ENDOSCOPE HAVING A LASER RADIATION SOURCE

This application is a continuation-in-part of application Ser. No. 07/781,585, filed Oct. 23, 1991 and now abandoned.

BACKGROUND OF THE INVENTION a) Field of the Invention

The present invention relates to a measuring endoscope, which may be inserted in narrow spaces such as interiors of organs of human bodies and interiors of industrial appliances for measuring concavities and convexities on the surfaces thereof.

b) Description of the Art

There is conventionally known a measuring endoscope which allows measurements of concavities and convexities on surfaces of organs of human bodies and so on by utilizing linear diffraction patterns of laser light formed with a diffraction grating. These diffraction patterns are projected onto a surface of an object to be observed by a projector lens for forming an image of the object. When this image is observed with parallax on an imaging device such as a solid-state image pickup device, the original linear diffraction patterns are deformed on the image of the object depending on shapes of the concavities and convexities on the surface. Accordingly, the measuring endoscope permits measuring the shapes of the concavities and convexities on the surface of the observed object by calculating, on the basis of video signals provided from the imaging device, displacement of lightness on each portion of the diffraction patterns on the surface of the object from lightness on a standard point.

Further, there is available the fringe scanning method as a method for measuring surfacial shapes of objects. This measuring method features high measuring accuracy, allows measurement independent of nonuniformities in contrast and permits automatic discrimination between concavities and convexities. Though the fringe scanning method is adopted for inspecting shapes of optical elements such as lenses, it is considered adequate to apply the projection type fringe scanning method to the measuring endoscope since this application makes it possible to obtain information on concavities and convexities which are not influenced by discoloration on diseased locations.

However, the measuring endoscope of this type poses a problem that it does not permit accurate measurement of surfacial shapes when the linear diffraction patterns are non-uniform in contrast due to colors, depths of concavities and convexities, etc. on the surfaces of objects to be measured. Further, there have been no conventional examples to apply the projection type fringe scanning method to measurements of shapes of objects within narrow spaces or to compact optical systems having small diameters such as endoscopes.

SUMMARY OF THE INVENTION

In view of the problems described above, it is a primary object of the present invention to provide a measuring endoscope which is capable of measuring concavities and convexities on surfaces of objects without being influenced by non-uniformities in contrast of the measuring light.

In order to solve the problem of the prior art, the present inventors devised a measuring means shown in FIG. 1. In this drawing, the reference numeral 1 represents a light source for emitting a laser beam B, the reference numerals 2 and 3 designate lenses which compose a beam expander for expanding the laser beam B, the reference numeral 4 denotes a beam splitter for splitting the expanded laser beam, the reference numeral 5 represents a fixed reflecting mirror for reflecting a beam which has been reflected by the beam splitter 4, the reference numeral 6 designates a movable reflecting mirror which functions to reflect a beam having passed through the beam splitter 4 and is disposed at an adequate inclination angle relative to the axis of incident light, the reference numeral 7 denotes an electrostrictive strain element which is capable of displacing the movable reflecting mirror 6 along the axis of incident light under control by a computer to be described later, and the reference numeral 8 represents a projector lens for expanding the two beams which have been reflected by the reflecting mirrors 5, 6 and overlapped with each other in the beam splitter 4 so that the two beams having passed through the projector lens 8 will form an optical field having variations in light intensity due to interference. The reference numeral 9 represents an object to be measured, which is placed at a measuring position in the optical field so that a surface 9a thereof is irradiated with the two beams having passed through the projector lens 8 and interference fringes 10 appear on the surface 9a due to the variation in the light intensity. These fringes are referred to as young fringes which are nearly linear fringes within an area not far from the optic axis of the illuminating light when the surface 9a of the object to be measured is plane. When the movable mirror 6 is displaced by the electrostrictive strain element 7, phase of the interference light changes on the surface 9a and the interference fringes are displaced in the direction perpendicular thereto. The numeral 11 represents a camera or an imaging device reference which is disposed at a predetermined angle relative to the surface 9a of the object to be measured 9 and used for imaging the interference fringes 10 or variations thereof, and the reference numeral 12 designates a computer which calculates depth or concavity or convexity from the variation in light height of a intensity at each point on the surface 9a of the measured object on the basis of video signals read out by the camera 11 and outputs calculation result of depth or height.

The measuring endoscope according to the present invention measures concavities and convexities according to the principle of the fringe scanning method as described above.

Now, the principle of the fringe scanning method adopted for the calculation by the computer 12 will be described below.

When the interference fringes produced by two beams which have an intersecting angle $\alpha$ therebetween are projected at an angle of incidence $\Theta$ onto the surface of the object to be measured having measuring points on the surface expressed by the x-y coordinates, the interference fringes are deformed depending on shape $f(x,y)$ of the surface and light intensity distribution $In(x,y)$ on the surface is given by the following formula:

$$In(x,y) = a(x,y) + b(x,y) \cos[2\pi(x/d_x + \Phi(x,y)) - \Phi_n] \qquad (1)$$

wherein $a(x,y)$: Average light intensity $b(x,y)$: Contrast of the fringes $\Phi_n$: Initial phase of interference light $d_x$: Interval between fringes in x direction (on the surface of the measured object)

$\Phi(x,y)$: Function related to concavity or convexity on surface

Further, $d_x$ is given by the following formula:

$$d_x = d/\cos\Theta = \lambda/[2\sin(\alpha/2)\cos\Theta] \quad (2)$$

wherein
d: interval between fringes.

Furthermore, the function $\Phi(x,y)$ related to concavity or convexity on surface used in formula (1) can be expressed as:

$$\Phi(x,y) = f(x,y)\sin\Theta/d \quad (3)$$

By scanning the interference fringes on the surface, it is possible to measure information on the function $\Phi(x,y)$ related to concavity or convexity on surface used in the formula (1) separately from $a(x,y)$ and $b(x,y)$ which represent nonuniformity in contrast.

When using four different interference light intensity distributions which are obtained by changing the initial phase in steps of 90° to the phase expressed by the following formula:

$$\Phi_n = n\pi/2 \, (n=0,1,2,3) \quad (4)$$

the argument of $\cos[2\pi(x/d_x + \Phi(x,y)) - \Phi_n]$ used in formula (1) can be expressed as follows:

$$2\pi(\Phi(x,y) + x/d_x) = \tan^{-1}[(I_1-I_3)/(I_0-I_2)] \bmod 2\pi \quad (5)$$

Since the phases obtained in this case have discontinuous values within a range from 0 to $2\pi$, these phases are connected smoothly by adding and subtracting $2\pi$ before and after the discontinuous points. Further, the second term $x/d_x$ in the left side of formula (5) can easily be removed from $\Phi(x,y)$ since this term varies uniformly relative to the x axis and it is possible to obtain the shape of the surface $f(x,y)$ by using formula (3).

In the measuring endoscope according to the present invention which has the configuration described above, the laser beam L emitted from the light source 1 passes through the lenses 2,3 and is expanded to an adequate size, where after a fraction of the laser beam L is reflected by the beam splitter 4 and reflected again by the fixed reflecting mirror 5. The rest of the laser beam L passes through the beam splitter 4 and is reflected by the movable reflecting mirror 6 at a predetermined angle relative to the axis of the incident light. The beam which has been reflected by the reflecting mirror 5 passes through the beam splitter 4, whereas the beam which has been reflected by the reflecting mirror 6 is reflected by the beam splitter 4, whereafter these beams are overlapped with each other, transmit through the projector lens 8 and irradiate the surface 9a of the object to be measured 9 with a predetermined intersecting angle. Accordingly, the two beams interfere with each other so as to form nearly linear interference fringes on the surface 9a, but actually the interference fringes appearing on the surface 9a are deformed depending on concavities and convexities thereon. These interference fringes 10 are imaged by the camera 11. When the electrostrictive strain element 7 is actuated and the movable reflecting mirror 6 is displaced along the axis of the incident light by energizing from the computer 12, the phase of the beam reflected by the reflecting mirror 6 is changed on the surface 9a of the object to be measured, whereby the interference fringes 10 are scanned in the direction perpendicular thereto. Variations of the fringes 10 or those of light intensity are read by the camera 11 and input to the computer 12. After the scanning of the interference fringes, depths and heights of concavities and convexities at individual points are calculated from the variations of light intensity at the individual points on the surface 9a by the calculation formula according to the fringe scanning method described above.

The measuring endoscope according to the present invention, which is based on the principle described above, is capable of measuring concavities and convexities on the surface 9a by utilizing the variations of light intensity produced by scanning the interference fringes regardless of nonuniformity in contrast caused by colors and depths of concavities and convexities on surfaces of measured objects, and permits automatic discrimination between concavity and convexity.

However, the measuring means mentioned above could not be used in the endoscope as it is. This is because when the measuring means is provided adjacent to the illumination optical system and the photographic optical system of the endoscope, as shown in FIG. 2, the diameter of the endoscope will increase dramatically. Further, the measuring means, which must scan the interference fringes, also requires space enough to move the reflecting mirror 6 and the electrostrictive strain element 7, as indicated by a double-pointed arrow, from dotted lines to solid lines. Consequently, the endoscope must be provided with a larger diameter.

Such an increase in diameter of the endoscope enables the measurement but serves no practical use. The endoscope, as illustrated in FIG. 3, has an illumination optical path for illuminating the inside of a dark hole and an observation optical path for observing the distal end. The illumination optical path is provided with a light source for illumination, for example, on the operator side of the endoscope, so that illuminated light is transmitted, by a light guide fiber bundle, from the control part of the endoscope through its insertable part to its tip distal end. The illuminated light is expanded by the illumination optical system at the tip of the endoscope and is irradiated on an object inside the hole. On the other hand, the observation optical path forms an image of the object through an objective optical system provided nearly parallel with the illumination optical system, for example, at the tip of the endoscope. This imaging plane is set by the entrance surface of an image guide fiber bundle for transmitting the image. The image guide fiber bundle transmits the image from the tip distal end of the endoscope through the insertable part to the control part. The transmitted image is received by a CCD situated in the control part of the endoscope and, after being processed by a computer, is observed through a TV. Also, the endoscope mentioned above is merely shown as an example, to which the present invention is not limited.

The appearance of the endoscope is shown in FIG. 4. Since the control part of such a long endoscope has a portion which is not inserted in the hole, it is not much limited by the diameter. The tip distal end and insertable part, however, are inserted in a narrow hole for observation, and as such it is required by the industrial field that they be fabricated as fine as possible.

In particular, an endoscope for medicine, illustrated in FIG. 5, is adapted to observe the affected parts of the stomach and intestines of a patient from his mouth through the gullet. Thus, since the size of the diameter of the endoscope causes pain to the patient, it is required that the endoscope have the smallest possible diameter.

In response to the particular need of such industrial fields of the endoscope, the inventors have made extensive improvements, with the arrangement shown in FIG. 1 as a step, and have completed the present invention.

The measuring endoscope according to the present invention includes an endoscope comprising an illumination optical path having an illumination light source provided as a light source for illuminating an object; illumination light transmitting means, composed of a plurality of optical fibers whose longitudinal directions coincide with one another, for transmitting light from the illumination light source; a plane of emergence for irradiating the object with the light from the illumination light transmitting means; an observation optical path having an objective lens for forming an image of the object with the light reflected from the object; image transmitting means, provided nearly parallel to the illumination light transmitting means, for transmitting the object image; observing means for observing the object image transmitted by the image transmitting means; a tip distal end including the plane of emergence of the illumination optical path and the objective lens of the observation optical path; an insertable part whose one end is connected with the tip distal end, extending lengthwise in a longitudinal direction along the illumination light transmitting means and the image transmitting means to be inserted in a narrow space, the insertable part including the illumination light transmitting means of the illumination optical path, and the image transmitting means of the observation optical path; and a control part connected with the other end of the insertable part for controlling the tip distal end and the insertable part.

According to one aspect of the present invention, the measuring endoscope includes a laser radiation source; phase difference changing means connected inside the control part or with the control part so that an optical path length of one polarized component in at least one direction, of light emitted from the laser radiation source, is changed with respect to the optical path length of the other polarized component in the other direction perpendicular to the direction of the one polarized component, and thereby a phase difference between two polarized components perpendicular to each other is changed with respect to time; a single optical fiber provided nearly parallel to the illumination light transmitting means and the image transmitting means in the insertable part of the endoscope, for transmitting beams of light with the phase difference caused by said phase difference changing means to the tip distal end of the endoscope; interference fringe producing means provided in the tip distal end of the endoscope, for producing interference fringes on a surface of the object from the light with the phase difference between the two polarized components perpendicular to each other which are transmitted by the single optical fiber; and processing means for calculating a profile of the surface of the object from an image of the interference fringes produced on the surface of the object which are transmitted, together with the object image, by the image transmitting means of the observation optical path, so that the phase difference is changed with respect to time by the phase difference changing means and thereby the interference fringes are scanned.

According to another aspect of the present invention, the measuring endoscope includes a laser radiation source; polarization state changing means connected inside the control part or with the control part, for changing a polarization state of a beam of light emitted from the laser radiation source; a single optical fiber provided nearly parallel to the illumination light transmitting means and the image transmitting means in the insertable part of the endoscope, for transmitting the light beam changed with respect to time of the polarization state by the polarization state changing means to the tip distal end of the endoscope; interference fringe producing means provided in the tip distal end of the endoscope, for producing interference fringes on a surface of the object from the light changed with respect to time of the polarization state which is transmitted by the single optical fiber; and processing means for calculating a profile of the surface of the object from an image of the interference fringes produced on the surface of the object which are transmitted, together with the object image, by said image transmitting means of the observation optical path, so that the polarization state is changed with respect to time by the polarization state changing means and thereby the interference fringes are scanned.

According to still another aspect of the present invention, the measuring endoscope includes a laser radiation source; wavelength selective means connected inside the control part or with the control part, for changing a wavelength of a beam of light, with respect to time, emitted from the laser radiation source; a single optical fiber provided nearly parallel to the illumination light transmitting means and the image transmitting means in the insertable part of the endoscope, for transmitting the light beam changed in wavelength by the wavelength selective means to the tip distal end of the endoscope; interference fringe producing means provided in the tip distal end of the endoscope, for producing interference fringes on a surface of the object from the light whose wavelength is changed with respect to time which is transmitted by the single optical fiber; and processing means for calculating a profile of the surface of the object from an image of the interference fringes produced on the surface of the object which are transmitted, together with the object image, by the image transmitting means of the observation optical path, so that the wavelength selective means and thereby the interference fringes are scanned.

Next, reference is made to the function of the measuring endoscope according to the present invention. The measuring endoscope is designed so that the scanning means shown in FIG. 2 is removed from the tip distal end of the endoscope and its diameter is made smaller. In FIG. 2, the optical path difference is provided between two beams of light split by the beam splitter 4, the reflecting mirrors 5 and 6, and the electrostrictive strain element 7, and interference fringes are produced and projected through the projection lens 8 on the object. Thus, even though the beam splitter 4 is disposed in the control part of the endoscope and the projection lens in the tip distal end, there is no means of transmitting the interference fringes.

Specifically, a fiber bundle used as an image guide or light guide, as shown in FIG. 6, is composed of several tens of or several hundred single fibers, and individual fibers forms an image as pixels. Since each of the single fibers is such that its end is round, the end face of the fiber bundle of the image fibers, as shown in FIG. 7, is formed with bright parts transmitting light and dark parts surrounding them, and a resultant scattered image of the fringes is projected on the object.

For this respect also, the present invention has made improvements so that the optical path difference is caused between the polarizing components. Even though the polarizing components are recombined by the beam splitter, the interference fringes cannot be produced because the directions of polarization are different. Hence, they can be transmitted as mere light, and this is accomplished by one fiber. The light beam thus transmitted to the tip of the endoscope by one fiber causes its polarized components to coincide so that fringes are produced and projected on the object.

As mentioned above, the control part of the endoscope is provided with much space required to produce the interference fringes, and in view of the transmission of light to the tip of the endoscope, the optical path difference is made between the polarized components. Thus, the interference fringes are derived from the arrangement having no space for the coincidence between the polarized components at the tip of the endoscope. Further, since the fringes are not produced at the tip of the endoscope, it is only necessary to use a single fiber as the transmitting means, with the resultant smaller diameter of the endoscope.

This and other objects as well as the features and the advantages of the present invention will become apparent from the following detailed description of the preferred embodiments when taken in conjunction with the accompanying drawings.

BRIEF DESCRIPTION OF THE DRAWINGS

FIGS. 2 through 7 are explanatory views relative to FIG. 1;

FIG. 9 is a diagram illustrating an end surface of a polarization maintaining fiber used in Embodiment 1;

FIG. 10 through FIG. 12 are views showing configurations of Embodiments 2 through 4;

FIG. 13 is a sectional view illustrating a fundamental configuration of Embodiment 5 of the measuring endoscope according to the present invention;

FIG. 15 shows diagrams illustrating variations of polarized conditions on the optical elements shown in FIG. 14;

DESCRIPTION OF THE PREFERRED EMBODIMENTS

Now, the measuring endoscope according to the present invention based on the principle described above will be explained in more detail with reference to the preferred embodiments illustrated in FIG. 8 through FIG. 26.

Figure 8:
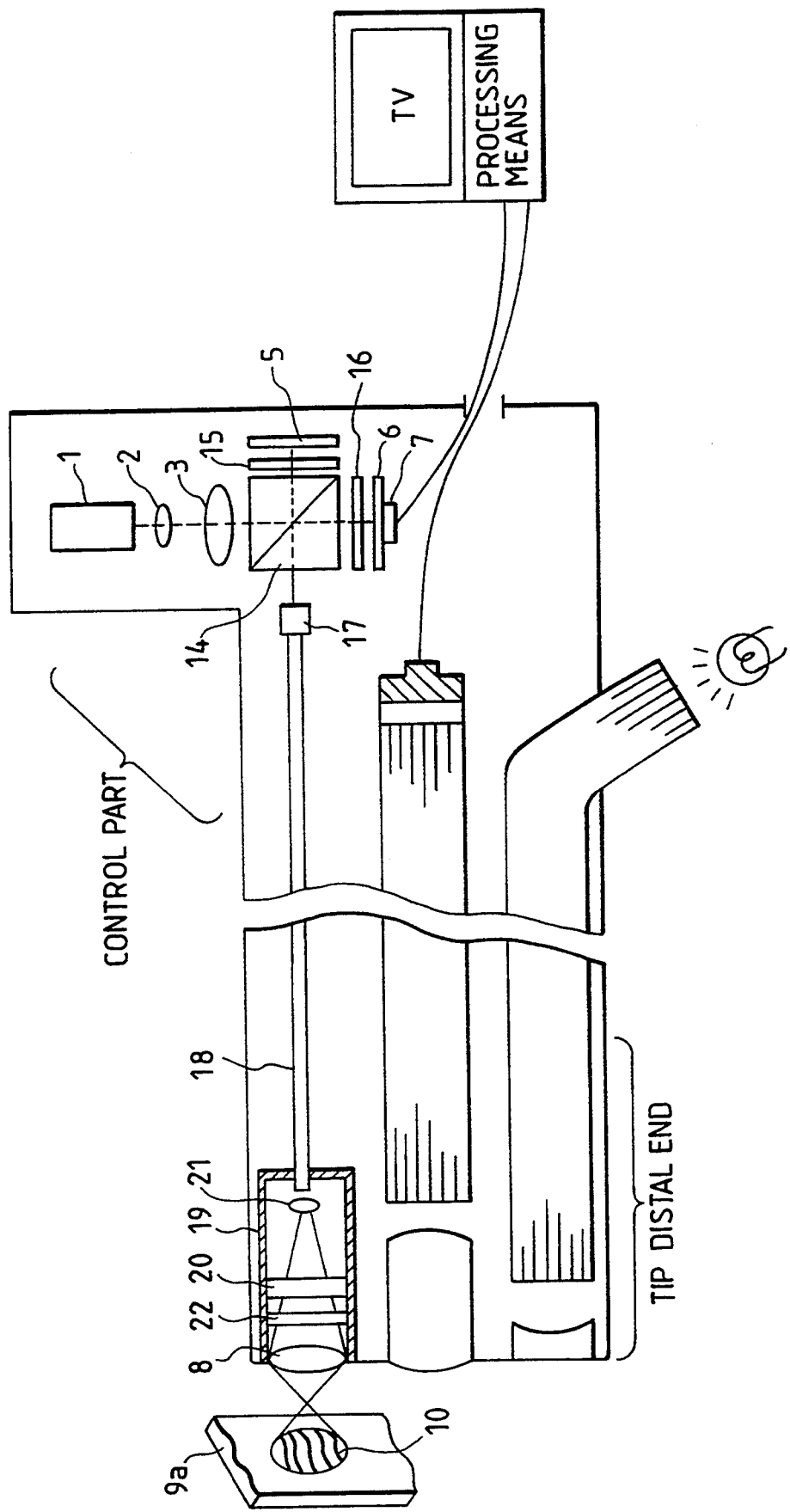
FIG. 8 is a schematic diagram illustrating a configuration of according to the present Embodiment 1 of the measuring endoscope invention, with an object, a camera and so on omitted.

FIG. 8 shows a schematic diagram illustrating a configuration of a straight view type endoscope of Embodiment 1 of the measuring endoscope according to the present invention, with the object to be measured 9, camera 11 and so on omitted. In this drawing, the reference numeral 14 represents a polarizing beam splitter for splitting a light beam emitted from the light source 1 into two polarized light beams, and reference numeral 15 designates a quarter wave plate which is arranged between the polarizing beam splitter 14 and the fixed reflecting mirror 5 so that the polarized component reflected by the polarizing beam splitter 14 will be polarized by twice transmission through the quarter wave plate 15 while it travels between the fixed reflecting mirror 5 and the polarizing beam splitter 14, and then the polarized component will be transmitted through the polarizing beam splitter 14. The reference numeral 16 denotes another quarter wave plate which is arranged between the polarizing beam splitter 14 and the movable reflecting mirror 6 so that the other polarized component will be polarized by twice transmission though the quarter wave movable reflecting plate 16 while it travels between the 6 and the polarizing beam splitter 14, whereafter the polarized component will be reflected by the polarizing beam splitter 14 and overlapped with the polarized component described above. The reference numeral 17 represents a coupler lens allowing transmission of the two beams which have been overlapped with each other by the polarizing beam splitter 14. The reference numeral 18 designates a polarization-maintaining fiber having an end connected to the coupler lens 17 and the reference numeral 19 denotes a head connected to the other end of the fiber 18. The reference numeral 20 represents a double image prism which is arranged before a lens 21 in the head 19. Since the two beams led from the polarizing beam splitter 14 to the polarization maintaining fiber 18 have directions of polarization perpendicular to each other and the double image prism 20 has a crystallographic axis so adjusted as to provide one of the polarized beams as the ordinary ray and the other polarized beam as the extraordinary ray, the double image prism 20 laterally displaces the other polarized beam only. Owing to this function of the double image prism 20, a difference in travelling direction is produced between the two beams which are to pass through the projector lens 8 and irradiate the object to be measured. Further, the reference numeral 22 represents a polarizing plate which is arranged between the double image prism 20 and the projector lens 8, and allows transmission of only the pure polarized components precisely perpendicular to each other contained in the two beams.

The cross section of the polarization-maintaining fiber 18 is shown in FIG. 9. The polarization-maintaining fiber 18 is usually provided with stress applying portions 18a and 18b around a core 18c and can transmit linearly polarized light in the x and y directions. Specifically, in the present invention, since the phase difference for producing interference fringes is provided between light beams with different directions of polarization, the interference fringes are not produced even though the light beams overlap as they are. Hence, it is only necessary to transmit the polarization of light beams in different directions, without any change, with the polarization-maintaining fiber 18 which is a single fiber. In order to produce the interference fringes with the linearly polarized light in the x and y directions, the double image prism 20 and the polarizing plate 22 cause the directions of polarization to coincide with each other.

In the present invention, the phase difference necessary for producing interference fringes is provided in the control part of the endoscope on the operator side, and at the same time, actual interference fringes are produced at the tip distal end of the endoscope. Thus, the scanning of interference fringes, namely a change of the amount of phase difference, is performed by the electrostrictive element 7 provided in the control part.

In addition, it is possible to select such an internal composition for the head 19, in place of the composition described above, that the two beams emerging from the fiber 18 are split again into two optical paths by a polarizing device such as a polarizing fiber coupler or a polarizing beam splitter and directions of polarization of the two beams are made coincident by rotating one of the beams for projecting the interference fringes onto the surface 9a of the object to be measured.

As is understood from the foregoing description, the measuring means preferred as the Embodiment of the present invention can be used in an endoscope which must comprise a compact optical system having a small diameter.

A side view type endoscope of Embodiment 2 of the present invention is illustrated in FIG. 10. In this embodiment, the image transmitting means of the observation optical system is constructed so that image information photoelectrically converted by the CCD disposed at the image plane of the objective lens is transmitted, by a cord, through the insertable part of the endoscope to the control part on the operator side. The cord is connected to the processing means for observation through the TV. The reference numeral 23 represents a light source which is capable of changing wavelength of light emission such as a color pigment laser, F center laser or thermally stabilized semiconductor laser, the reference numeral 23a represents a wavelength changing device, the reference numeral 24 designates an optical fiber for leading the light beam, which is emitted from the light source from the coupler lens 17 to a head 25, the reference numeral 26 denotes a lens which is arranged in the head 25 and functions to convert the light emerging from the optical fiber into plane waves, the reference numeral 27 represents a beam splitter which is slightly inclined relative to the optic axis of the plane wave indent thereon, and the reference numeral 28 designates a reflecting coat which is attached to two neighboring side surfaces of the beam splitter 27, and has two surfaces 28a, 28b for reflecting the beam having passed through the beam splitter 27 and the beam having been reflected by the beam splitter 27 respectively. These surfaces 28a, 28b are located at different distances as measured from the light splitting point of the beam splitter 27 so that a difference in phase is produced between the two beams reflected by the reflecting coat 28.

In Embodiment 2, a fraction of the light incident on the beam splitter 27 is reflected by the beam splitter 27 and reflected again by the surface 28b of the reflecting coat 28, whereas the remaining fraction of incident light passes through the beam splitter 27 and is reflected by the surface 28a of the reflecting coat 28, whereafter these lights are overlapped with each other and travel to the projector lens 8. Travelling directions of the two beams deviate from each other depending on the inclination angle of the beam splitter 27. A difference in phase is produced by the reflections on the surfaces 28a, 28b of the reflecting coat 28. Accordingly, the interference fringes 10 are projected to the surface 9a of the object to be measured 9 through the projector lens 8. The interference fringes are scanned by changing the wavelength of the light beam emitted from the light source 23 so as to vary the difference in phase between the two beams, which produce the interference fringes.

In Embodiment 2 also, only the head 25 and the optical fiber 24 are arranged in an endoscope, whereas the light source 23 and the wavelength changing device 23a are disposed outside the endoscope.

Embodiment 2 has an advantage that it permits designing the measuring means more compactly than that obtainable by Embodiment 1 and another advantage that the projected interference fringes and scanning of the fringes are stabilized against external influences since the distance as measured from the light splitting point to the irradiation point with the interference fringes is shorter in Embodiment 2 than that in Embodiment 1. In addition, the interference fringes can be formed more efficiently by using a polarizing beam splitter in place of the beam splitter 27, and interposing a quarter wave plate between the polarizing beam splitter and the surface 28a of the reflecting coat 28, and another quarter wave plate between the surface 28b and the polarizing beam splitter. In such a case, it is necessary to interpose a polarizing plate between the polarizing beam splitter and the projector lens 8.

Figure 11:
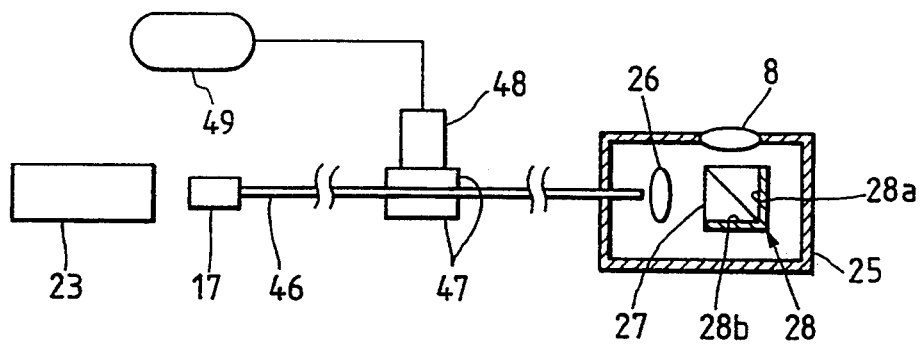

FIG. 11 is a schematic diagram description of Embodiment 3 of the present invention. In this figure, the same side view type endoscope as in FIG. 10 is shown and hence, the arrangements of the illumination and observation optical systems are omitted. A light beam emitted from the light source 23, which consists, for example, of a color pigment laser, F center laser or thermally stabilized semiconductor laser which is capable of changing wavelength, is led to the coupler lens 17. In FIG. 11, the reference numeral 46 represents a multi-mode fiber into which the light beam emitted from the light source 23 is led through the coupler lens 17, the reference numeral 47 designates two plane plates used for fixing the multi-mode fiber under pressure, the reference numeral 48 denotes an electrostrictive strain element having an end attached to the plane plate 47, and the reference numeral 49 represents a driving circuit for applying a high-frequency voltage to the electrostrictive strain element 48.

Accommodated in the head 25 connected to the other end of a multi-mode fiber are the lens 26 for converting the beam emerging from the multi-mode fiber 46 into plane waves, the beam splitter 27 arranged slightly inclined relative to the optic axis of the plane wave, the reflecting coat 28 having the reflecting surfaces 28a, 28b which are arranged on side surfaces located at distances different from each other as measured from the beam splitting point in the beam splitter 27 and function to produce a difference in phase between the beams reflected by the reflecting surfaces, and the projector lens 8.

In Embodiment 3, the interference fringes are scanned by changing wavelength of the light beam emitted from the light source 23 so as to vary the difference in phase between the two beams which produce the interference fringes.

When the multi-mode fiber 46 is adopted, however, the light beam emerging therefrom contains speckle patterns which are produced by the modal interference component. When such a beam is used for forming the interference fringes on the surface of the object to be measured, light intensity distribution will be as if it were that on the linear interference fringes overlapped with the speckle patterns. Such a light intensity distribution will degrade measuring accuracy. In order to prevent such degradation of measuring accuracy, Embodiment 3 adopts an electrostrictive strain element 48 which averages the speckle patterns by changing refractive index in the multi-mode fiber 46. When the electrostrictive strain element 48 is driven with the driving circuit 49, strain thereof is applied to the multi-mode fiber 46, whereby the refractive index in the multi-mode fiber 46 is changed periodically so as to average the modal interference component with time which is produced in the multi-mode fiber 46.

The light beam emerging from the multi-mode fiber 46 is split in two by the beam splitter 27, whereafter these two beams are overlapped with each other and travel toward the projector lens 8. In this course, traveling directions of the two beams deviate from each other depending on the inclination angle of the beam splitter 27 and a phase difference is produced by the reflections on the surfaces 28a, 28b of the reflecting coat 28. Accordingly, linear interference fringes are projected to the surfaces of the object to be measured through the projector lens 8.

Embodiment 3, which uses the multi-mode fiber 46 as a light guide, permits utilizing light more efficiently than the measuring means using a single-mode fiber. Consequently, bright interference fringes can be derived.

Figure 12:
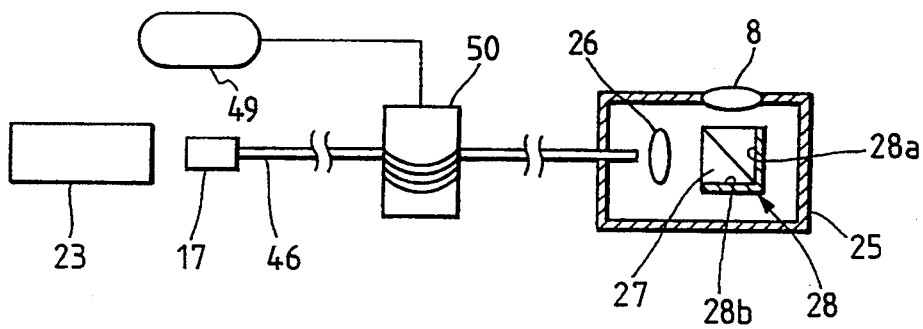

FIG. 12 shows a schematic diagram descriptive of Embodiment 4 of the present invention. In this figure, the same side view type endoscope as in FIG. 10 is shown and hence, the arrangements of the illumination and observation optical systems are omitted. Embodiment 4 uses the light source 23, the multi-mode fiber 46, the head 25 and the other members which are the same as those employed in Embodiment 3 described above, but adopts a different means for averaging the modal interference component with time. Speaking concretely, the embodiment 4 adopts, in place of the plane plates 47, the multi-mode fiber 46 which is wound several turns around an electrostrictive strain element 50. When a high-frequency voltage is applied to the electrostrictive strain element 50 from the driving correct 49, the electrostrictive strain element 50 elongates and contracts, thereby applying strain to the multi-mode fiber 46. Accordingly, the modal interference component is averaged with time in the multi-mode fiber 46. Embodiment 4, wherein strain is applied to the multi-mode fiber 46 longer than that used in Embodiment 3, permits averaging the modal interference component with a relatively low voltage.

FIG. 13 shows a schematic diagram descriptive of Embodiment 5 of the present invention. In this drawing, the reference numeral 51 represents a light source unit which emits a linearly polarized light and is so composed as to be capable of controlling azimuth of the linearly polarized light, the reference numeral 52 designates a quarter wave plate for changing a phase difference between polarized components which are perpendicular to each other and to the light emitted from the light source unit 51, the reference numeral 53 denotes a polarization-maintaining fiber, the reference symbol O represents an objective lens, and the reference symbol IG designates an image guide.

Embodiment 5 makes it possible to design the distal end of the endoscope in a compact manner and permits observing the produced interference fringes through the objective lens O, the image guide IG, the CCD and the TV, since it is adapted to perform the phase shift by transmitting the phase difference between the polarized components through the polarization-maintaining fiber 18 to the tip thereof and permit arranging the phase shifting means on the side nearer the operator. Further, Embodiment 5 provides other merits that the measuring endoscope according to the present invention can be simpler in the configuration thereof, manufactured at a lower cost, facilitated in the adjustment for condensing the light into the fiber and designed more easily as a commercial product since the externally arranged means for the phase shift is adapted not to compose the polarized components after the light is split into the polarized components and the phase difference is changed, but to change the phase difference in the original single light beam. The effect of Embodiment 5 remains unchanged even when the location of the quarter wave plate 52 is replaced with that of the polarization-maintaining fiber 18.

Figure 14:
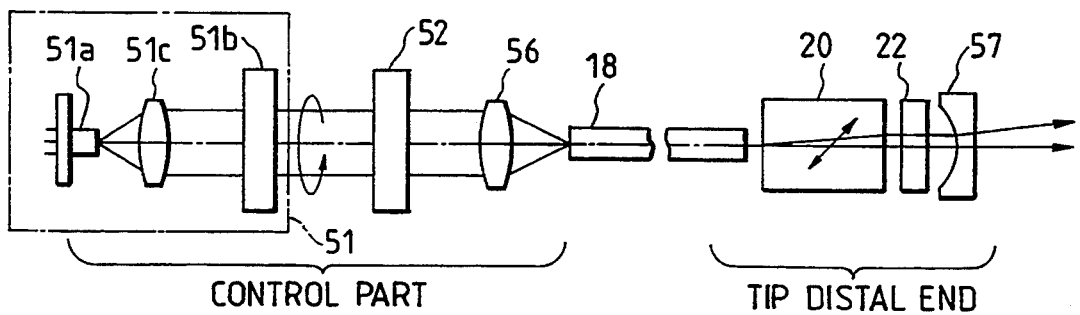
FIG. 14 is a schematic diagram illustrating a concrete configuration of Embodiment 5 of the measuring endoscope according to the present invention.

FIG. 14 illustrates a concrete example of the light source unit 51 which is composed of a light source 51a, such as a semiconductor laser or an He—Ne laser, which emits a linearly polarized coherent light beam and a half wave plate 51b adopted as an element controllable in the rotating direction thereof. In FIG. 14, the reference numerals 51c and 56 represent collimator lenses, and the reference numeral 57 designates a projector lens. In this figure, the same straight view type endoscope as in FIGS. 8 and 13 is shown and hence, the arrangements of the illumination and observation optical systems are omitted.

FIG. 15 visualizes variations of the polarized condition of the light beam obtained by the optical members illustrated in FIG. 14. Assuming that a linearly polarized light beam has an oscillating direction of 45°, this direction only is changed by an angle of 2 Θ after the linearly polarized light beam has passed through the half wave plate 51b. After passing through the quarter wave plate 52 which is set at an azimuth of 45° the polarized condition is changed as shown in FIG. 15. In this case, the azimuth 45° of the quarter wave plate means that the azimuth of the quarter wave plate is inclined 45° relative to the x,y polarization axes on the end surface of incidence of the polarization-maintaining fiber 18. On the other hand, the light beam emerging from the polarization maintaining fiber 18 is split into two by arranging, right after the exit end face of the polarization-maintaining fiber 18, a birefringent plate 20 having an optic axis which is inclined relative to the optic axis of the incident light beam but coincident with one of the x, y polarization axes on the exit end face of the polarization-maintaining fiber 18. Further, by arranging a polarizing plate 22 which has an axis of polarization inclined 45° relative to the optic axis of the birefringent plate 20, only coherent components contained in the two polarized components are taken out for forming interference fringes.

In the configuration described above wherein the rotated linearly polarized light beam which has passed through the half wave plate 51b transmits through the quarter wave plate 52, phases of the x and y components of the polarized light beam are changed continuously, and intensities of the x and y components are equal to each other and stabilized. This light beam transmits through the polarization-maintaining fiber 18 while the phase difference between the components of the x and y polarized wave axes remain unchanged. Accordingly, the change of phase difference between the x and y components, which is caused by rotating the half wave plate 51b provided on the side nearer the operator and allowing the transmission of the phase difference through the quarter wave plate 52, is transmitted to the exit end face of the polarization maintaining fiber 18, thereby making it possible to scan the interference fringes without mechanically moving the tip of the polarization-maintaining fiber 18. Further, Embodiment 5 has a simple configuration and permits composing the tip of the polarization-maintaining fiber in a compact manner.

Embodiment 5 makes it possible to compose the distal end of the endoscope compact and perform the phase control relatively easily since the phase shift is performed by rotating the half wave plate 51b provided as the phase shift means and transmitting the phase difference between the polarized components through the polarization-maintaining fiber to the exit end face thereof, and the phase shift means can be arranged on the side nearer the operator. Furthermore, since the phase shift means externally provided is adapted not to compose the polarized components after the light is split into the polarized components and the phase difference is changed, but to change the phase difference between the polarized components contained in the original single light beam, the measuring endoscope preferred as Embodiment 5 can be manufactured easily at low cost and facilitates condensing the light into the polarization-maintaining fiber.

Figure 16:
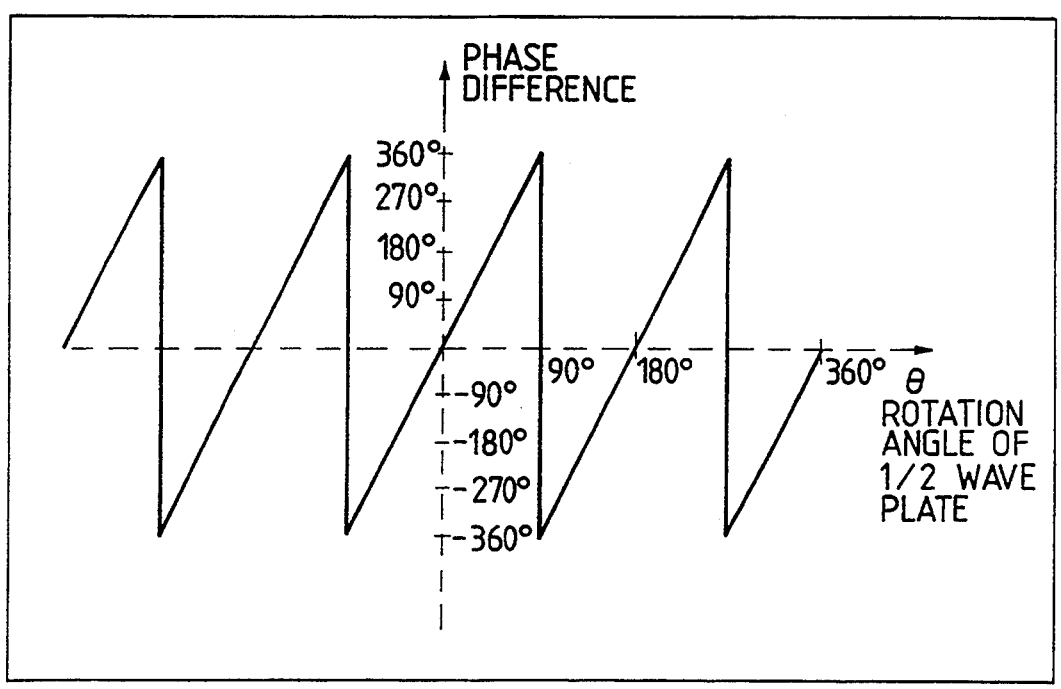
FIG. 16 is a graph illustrating variations of phase in Embodiment 5.
Figure 17:
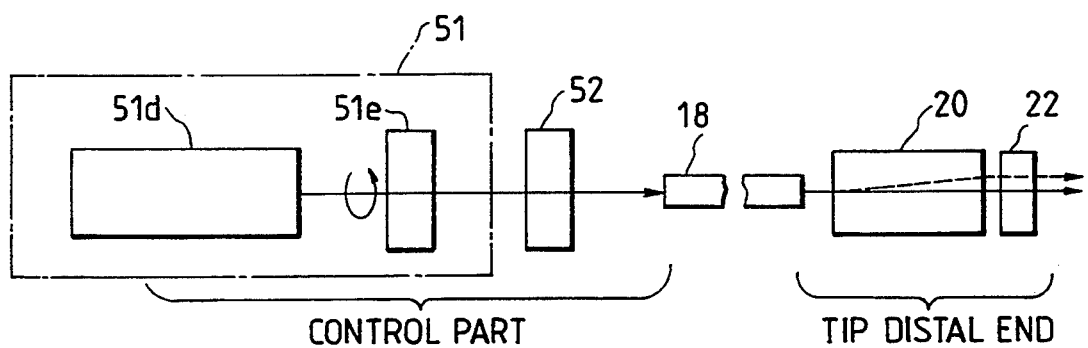
FIG. 17 through FIG. 22 are schematic diagrams illustrating modifications of Embodiment 5, which differ from one another.

The polarized conditions obtained in Embodiment 5 will be expressed by mathematical formulae below. These formulae will clarify the facts that the intensity of the interference fringes remains unchanged regardless of the rotating angle $\Theta$ of the half wave plate 51b and that only phases of the x and y components change at a speed of $4\Theta$. FIG. 16 visualizes the variations of the phases.

Polarized condition $\begin{bmatrix} Ex \\ Ey \end{bmatrix} = \begin{bmatrix} 1/\sqrt{2} \\ 1/\sqrt{2} \end{bmatrix}$ of laser beam Half wave plate at a $\overline{P} = \begin{bmatrix} \cos\theta & -\sin\theta \\ \sin\theta & \cos\theta \end{bmatrix} \begin{bmatrix} e^{i\pi} & 0 \\ o & 1 \end{bmatrix} \begin{bmatrix} \cos\theta & \sin\theta \\ -\sin\theta & \cos\theta \end{bmatrix}$ rotating angle of $\Theta$ Quarter wave plate at -continued $\overline{Q} = \begin{bmatrix} \cos\frac{\pi}{4} & -\sin\frac{\pi}{4} \\ \sin\frac{\pi}{4} & \cos\frac{\pi}{4} \end{bmatrix} \begin{bmatrix} e^{i\frac{\pi}{2}} & 0 \\ o & 1 \end{bmatrix} \begin{bmatrix} \cos\frac{\pi}{4} & \sin\frac{\pi}{4} \\ -\sin\frac{\pi}{4} & \cos\frac{\pi}{4} \end{bmatrix}$ an azimuth of 45°

$\begin{bmatrix} Ex' \\ Ey' \end{bmatrix} = \overline{Q} \cdot \overline{P} \cdot \begin{bmatrix} Ex \\ Ey \end{bmatrix}$ $= \overline{Q} \cdot \overline{P} \cdot \begin{bmatrix} 1/\sqrt{2} \\ 1/\sqrt{2} \end{bmatrix}$ $= \frac{1}{\sqrt{2}} \begin{bmatrix} -\cos^2\theta + \sin^2\theta - 2i\cos\theta\sin\theta \\ \cos^2\theta - \sin^2\theta - 2i\cos\theta\sin\theta \end{bmatrix}$ $= \frac{1}{\sqrt{2}} \begin{bmatrix} -\cos 2\theta - i\sin 2\theta \\ \cos 2\theta - i\sin 2\theta \end{bmatrix}$ $= \frac{1}{\sqrt{2}} \begin{bmatrix} -1 \cdot e^{i(2\theta)} \\ +1 \cdot e^{-i(2\theta)} \end{bmatrix}$ Phase difference: $2\Theta - (-2\Theta) = 4\Theta$ $|EX'| = 1/\sqrt{2} \quad |Ey'| = 1/\sqrt{2}$ In Embodiment 5, the angle between the polarization axis of the polarization-maintaining fiber 18 and the optic axis of the quarter wave plate 52 as well as the angle between the polarization axis and the optic axis of the birefringent plate 20 need not be set always at 45°, but no problem is posed so far as these angles are set equal to each other. Moreover, it is possible to perform stereoscopic measurements by stopping the half wave plate 51b provided as the phase shift means at phase positions of 0°, 90°, 180° and 270° which are shifted 90° from one another and inputting images of an object obtained at these phase positions into the computer 12 for analysis or by using integrated images of the object obtained at the phase positions while rotating the half wave plate continuously.

As the birefringent plate 20 having the crystallographic axis inclined relative to the optic axis which is used as the means for splitting the light beam into the respective polarized components in Embodiment 5, there are available birefringent crystals such as rutile, calcite, quartz and sapphire. Further, usable as the means for splitting the light beam into the polarized components are double image prisms such as Senarmont prisms (compensator), Rochon polarizing prisms and Wollaston prisms.

The light source unit 51, which emits the linearly polarized light beam and is capable of controlling azimuth thereof, is used in Embodiment 5. This light source unit may comprise a combination of a coherent light source 51d emitting circularly polarized light beam and a rotatable quarter wave plate 51e. When the coherent light source 51d is combined with the quarter wave plate 51e which is fixed at an angle of 45° interference fringes are set in the conditions expressed by the following formulae:

Circularly polarized $$\begin{bmatrix} Ex \\ Ey \end{bmatrix} = \begin{bmatrix} 1/\sqrt{2} \\ 1/\sqrt{2} \exp(\lambda\pi/2) \end{bmatrix}$$

light beam

Quarter wave plate at a rotating angle of Θ

$$\overline{R} = \begin{bmatrix} \cos\theta & -\sin\theta \\ \sin\theta & \cos\theta \end{bmatrix} \begin{bmatrix} e^{i\pi/2} & 0 \\ 0 & 1 \end{bmatrix} \begin{bmatrix} \cos\theta & \sin\theta \\ -\sin\theta & \cos\theta \end{bmatrix}$$

Quarter wave plate at $$\overline{R} = \begin{bmatrix} \cos\frac{\pi}{4} & -\sin\frac{\pi}{4} \\ \sin\frac{\pi}{4} & \cos\frac{\pi}{4} \end{bmatrix} \begin{bmatrix} e^{i\frac{\pi}{2}} & 0 \\ 0 & 1 \end{bmatrix} \begin{bmatrix} \cos\frac{\pi}{4} & \sin\frac{\pi}{4} \\ -\sin\frac{\pi}{4} & \cos\frac{\pi}{4} \end{bmatrix}$$

azimuth of 45°

$$\begin{bmatrix} Ex' \\ Ey' \end{bmatrix} = \overline{Q} \cdot \overline{R} \cdot \begin{bmatrix} Ex \\ Ey \end{bmatrix}$$

$$= \frac{1}{\sqrt{2}} \begin{bmatrix} -\cos 2\theta - i\sin\theta \\ -1 \end{bmatrix}$$

$$= \frac{1}{\sqrt{2}} \begin{bmatrix} e^{-i2\theta} \\ -1 \end{bmatrix}$$

Figure 18:
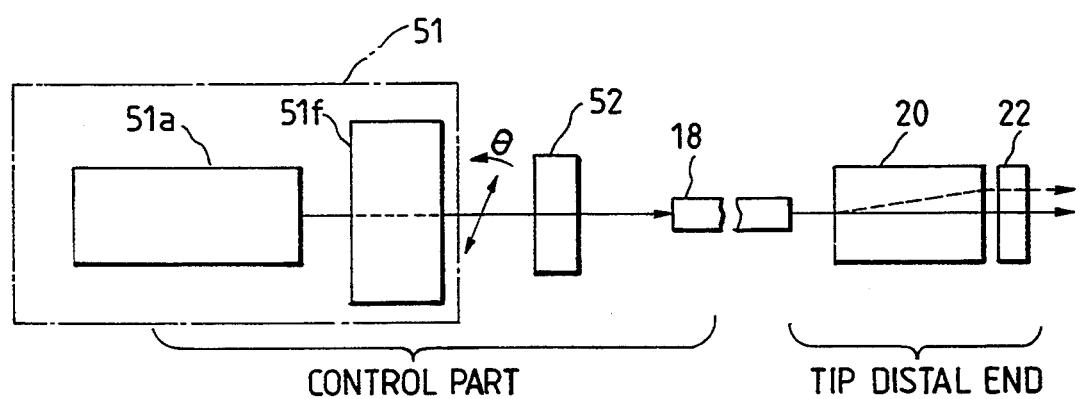
Figure 19:
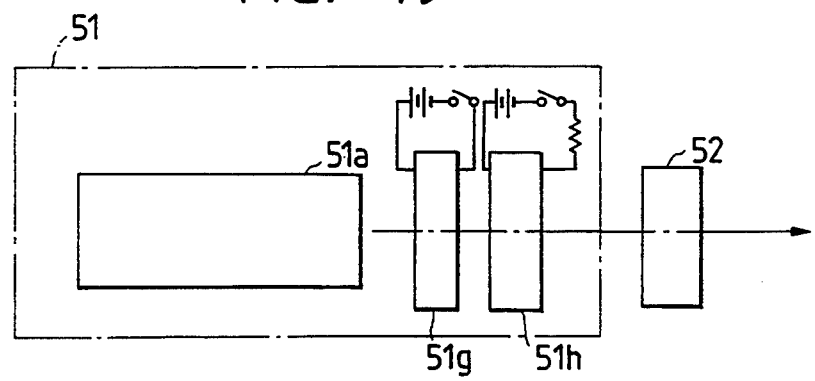

Phase difference:  $-2\Theta - 0 = -2\Theta$ $|EX'| = 1/\sqrt{2}$    $|Ey'| = 1/\sqrt{2}$ Furthermore, the light source unit 51 may comprise a combination of a laser light source 51a emitting a linearly polarized light and a Faraday effect element 51f as shown in FIG. 18. In this case, azimuth of the linearly polarized light can be controlled by adjusting the voltage applied to the Faraday effect element 51f. That is to say, this combination utilizes optical rotation of a crystal.

Moreover, the light source unit 51 may comprise a combination of the light source 51a emitting the linearly polarized light and two kinds of liquid crystal cells 51g, 51h. This is an example which utilizes the optical rotation of the liquid crystals and is adapted so as to be capable of changing azimuth of the linearly polarized light in four directions by turning on and off the power sources connected to the liquid crystal cells 51g, 51h. Speaking concretely, the liquid crystal cell 51g is utilized as an optical rotator which changes an angle of optical rotation from 0° to 45° by turning on and off the power source connected thereto, whereas the liquid crystal cell 51h functions as an optical rotator which changes an angle of optical rotation from 0° to 90° by turning on and off the power source connected thereto.

In addition, it is possible to mount the laser light source 51a properly, for example, on a rotating stand and change azimuth of the linearly polarized light by turning the laser light source 51a.

Next, description will be made of other examples of the retarder (an element which is capable of changing only phase without changing azimuth) which is typically represented by the quarter wave plate 52 shown in FIG. 13 through FIG. 19.

Figure 20:
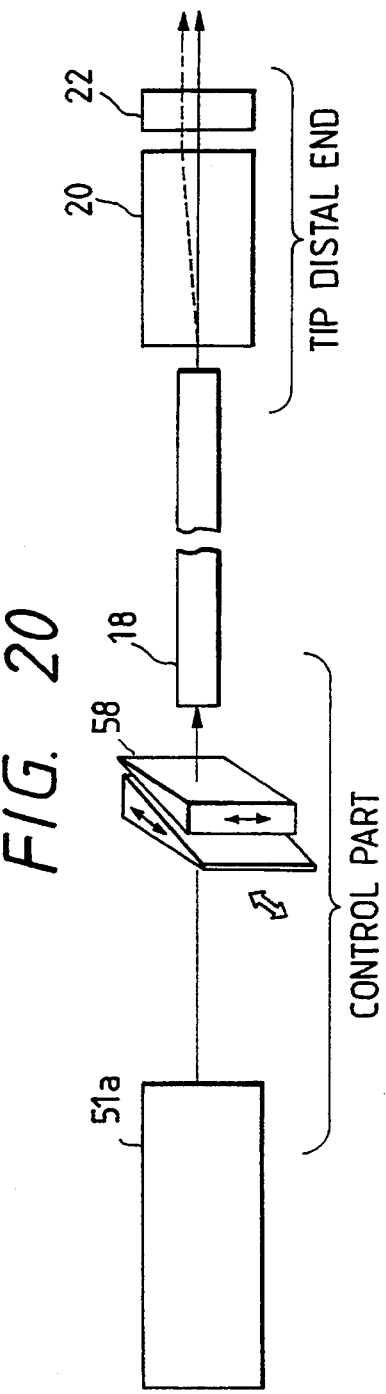

FIG. 20 shows an example wherein a Babinet-Soleil plate 58 is used as the retarder. In FIG. 20, the phase component can be changed by moving the Babinet-Soleil plate 58 in the direction (indicated by the thick arrows) perpendicular to the optic axis. This change of the phase component is transmitted through the polarization maintaining fiber 18 to the tip thereof, thereby making it possible to change the phase of the interference fringes to be formed.

Figure 21:
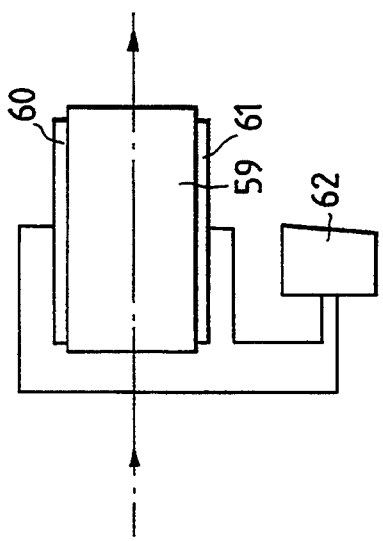

FIG. 21 shows another example wherein a crystal 59 having an electro-optical effect is used as the retarder. Crystal 59 may be formed of LiNbO$_3$, LiTaO$_3$, or KDP. When electrode plates 60 and 61 are arranged on both the sides of the crystal 59, a voltage controller 62 is connected to these electrode plates and an electric field is produced in the direction perpendicular to the optic axis, the difference in refractive index between directions of polarization perpendicular to each other is changed. The light beam having passed through the crystal 59 transmits the change of phase through the polarization-maintaining fiber 18 to the tip thereof and is separated into two polarized components by the birefringent plate 54, whereby the two beams form interferes fringes. When the voltage applied from the voltage controller 62 to the crystal 59 is changed, the interference fringes are scanned.

Figure 22:
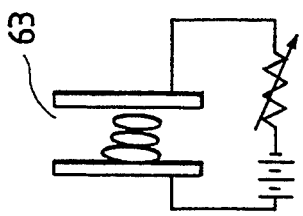

FIG. 22 shows still another example wherein a liquid crystal device 63 is used as the phase retarder. In this example, a phase difference between the polarized components contained in a light beam passing through the liquid crystal is changed depending on the level of the voltage applied to the liquid crystal and the change of the phase difference is transmitted through the polarization-maintaining fiber 18 to the tip thereof, whereby the interference fringes can be scanned as in the case of the example shown in FIG. 21. The example shown in FIG. 22, like the example illustrated in FIG. 21, permits arranging the voltage controller such as a variable resistor provided as the phase shifting means on the side nearer the operator, thereby providing not only a merit to permit compact design of the distal end of the measuring endoscope, but also other merits to permit simplifying configuration thereof and facilitating adjustment or control of the light beam incident on the polarization-maintaining fiber.

Figure 1:
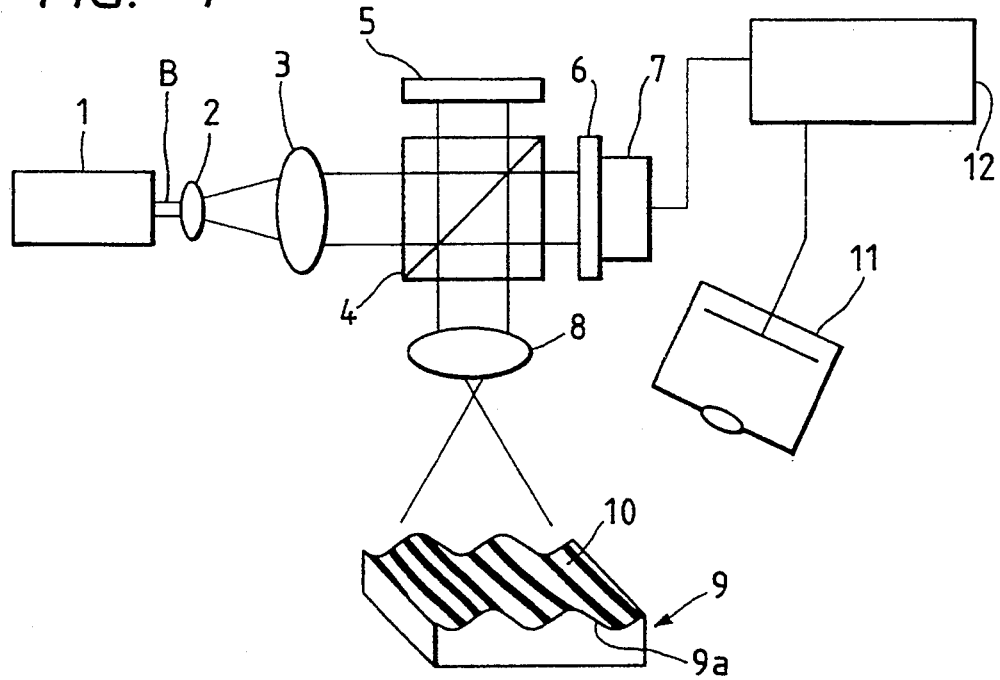
FIG. 1 is a conceptional view at a stage before the present invention is created.
Figure 2:
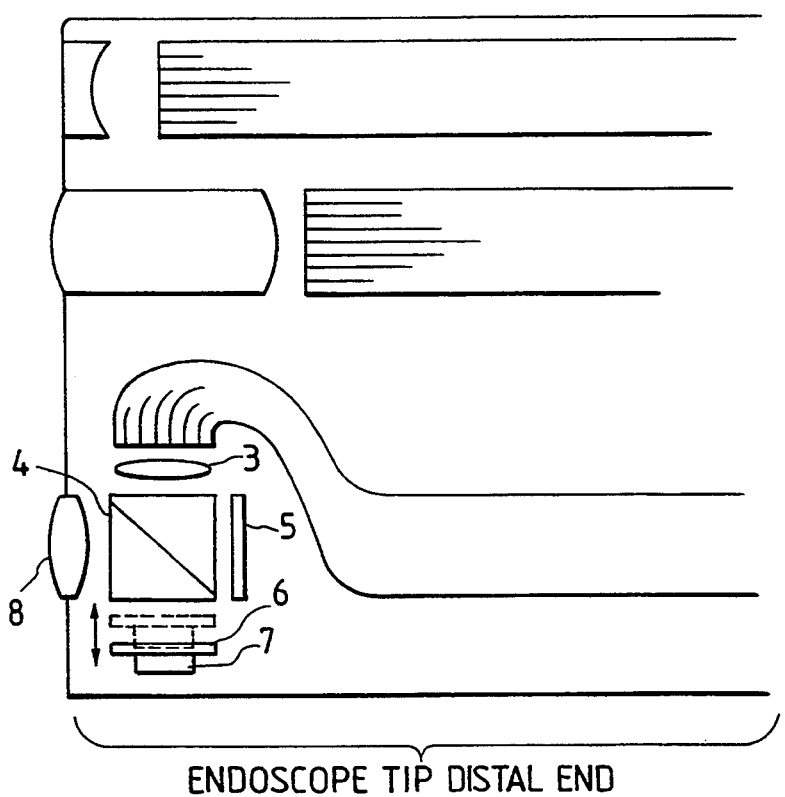
Figure 3:
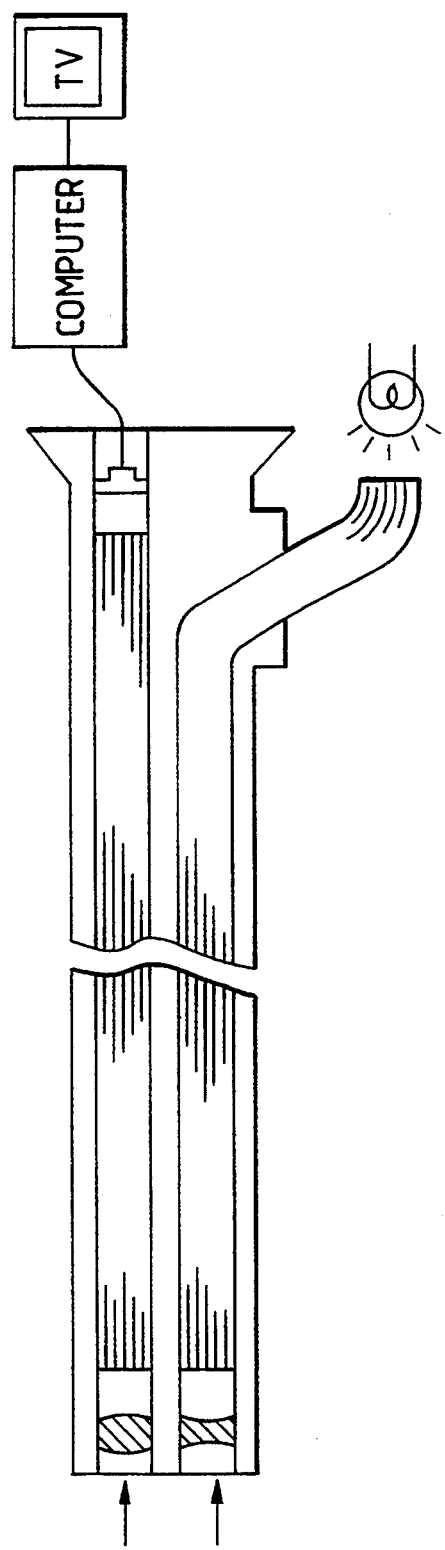
Figure 23:
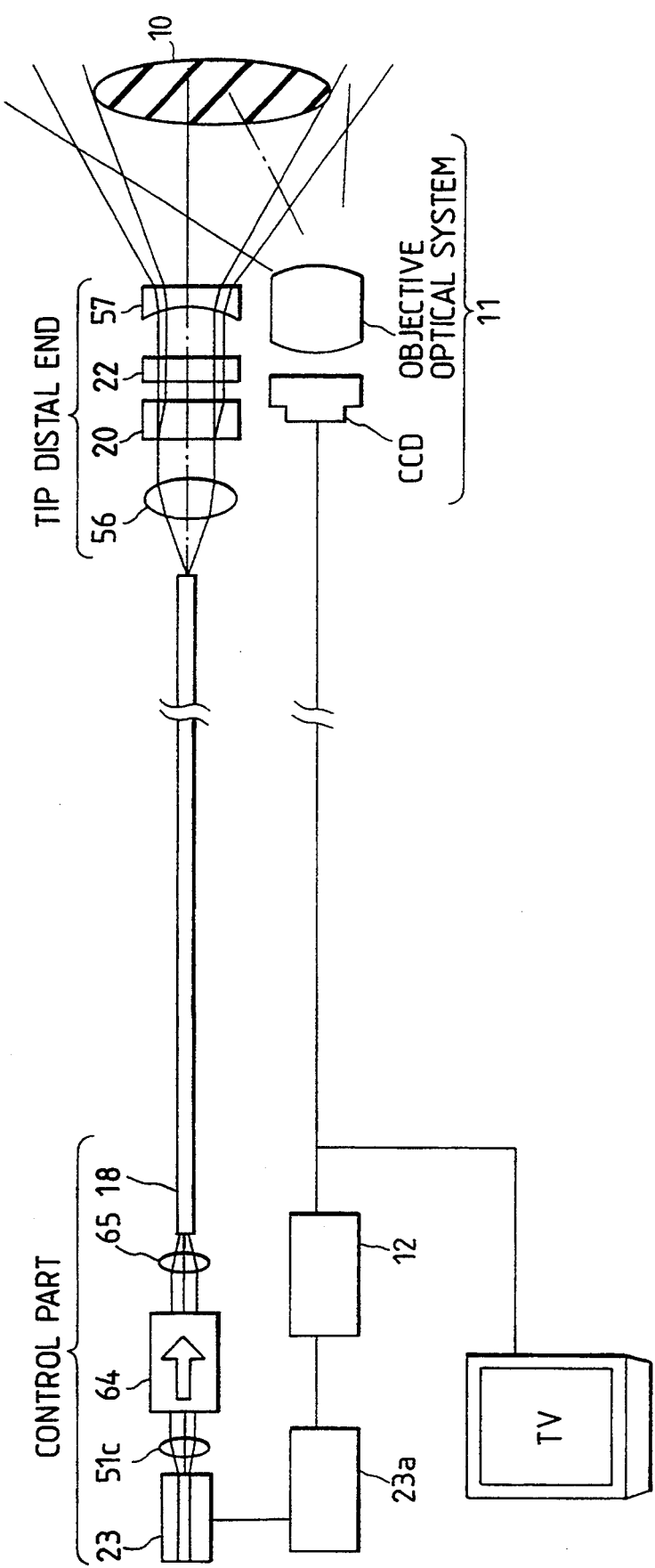
FIG. 23 a schematic diagram illustrating a configuration of Embodiment 6 of the measuring endoscope according to the present invention.

FIG. 23 is a schematic diagram descriptive of Embodiment 6 of the present invention. In this drawing, the reference numeral 64 represents an optical isolator, the reference numeral 65 designates a coupler lens, and the reference numeral 67 represents a fringe analyzer. The other component members of Embodiment 6 will not be described particularly since they are the substantially the same as those shown in FIGS. 1, 10 and 14, and represented by the reference numerals used in these drawings.

In Embodiment 6, an optical-path difference is produced between the polarized components perpendicular to each other by birefringence of the polarization-maintaining fiber 18 so as to reduce the distance of the phase shift. Accordingly, the two beams to interfere with each other travel along optical paths which are nearly coincident with each other, whereby interference fringes are nearly completely free from influences due to external disturbances. Further, the distal end of the endoscope can be made compact since it comprises no movable member.

In Embodiment 6, it is sufficient for obtaining a change of $2\pi$ in phase difference to satisfy the following formula:

$$2\pi = (2\pi\Delta\lambda/\lambda^2)L(n_x - n_y) \quad (6)$$

wherein the reference symbol $n_x$ represents the refractive index of the polarization-maintaining fiber 18 as measured in the x direction, the reference symbol $n_y$ designates the refractive index of the polarization-maintaining fiber 18 in the y direction, the reference symbol L denotes the length of the polarization-maintaining fiber 18, the reference symbol $\lambda^2$ represents the wavelength of the measuring light used and the reference symbol $\Delta\lambda$ designates the shift distance of wavelength.

From formula (6) above, the required distance of wavelength shift is:

$$\Delta\lambda = \lambda^2/[L(n_x - n_y)] \quad (7)$$

Hence, it is possible to apply the phase shift method when the wavelength of the light emitted from the light source is changed continuously or stepwise for the distance of wavelength shift determined by the formula (7).

A semiconductor laser or a pigment laser may be used as a wavelength variable light source. In particular, the semiconductor laser permits easily shifting wavelength of the light beam emitted therefrom by varying level of the current supplied thereto. Further, it is possible to perform the wavelength shift by combining a white light source and a variable wavelength filter.

In Embodiment 6, the light beam emitted from the semiconductor laser 51a is made by the collimator lens 51c into a parallel beam, which passes through the isolator 64 interposed for eliminating returning light. Then, the light beam passes through the coupler lens 65 and is incident on the polarization-maintaining fiber 18.

Assuming that the longitudinal direction of the polarization maintaining fiber 18 is inclined 45° relative to the direction of polarization of the incident laser beam, a phase difference is produced between the x polarized component and the y polarized component contained in the light beams having passed through the polarization-maintaining fiber 18. The light beams having passed through the polarization-maintaining fiber 18 are made by the collimator lens 56 into a parallel beam, which falls on the birefringent plate 20 such as a Wollaston prism. The birefringent plate 20 has a crystallographic axis which is coincident with either one of the two polarized components incident thereon. Accordingly, the other polarized component which is the extraordinary light for the birefringent plate 20 deviates from the crystallographic axis. Due to the transmission of these polarized components through the polarizing plate 22, linear interference fringes are formed. An image which is deformed depending on concavities and convexities on the surface of the object to be measured can be obtained by projecting these interference fringes through the projector lens 57 onto the surface of the object to be measured and imaging these fringes by the imaging device 11 such as a CCD camera. When the wavelength shift is performed, the phase difference between the two beams forming the interference fringes changes and the interference fringes are scanned. Images obtained in this manner are taken from the imaging device 11 into the range analyzer 67 and analyzed, whereby the concavities and convexities on the surface are measured.

The phase shift method utilizing the wavelength shift is not applicable to the interferometer using the birefringent plate 20 and the polarizing plate 22 which produces nearly no optical-path difference. As is clear from the foregoing description, however, the phase shift method utilizing the wavelength shift is applicable to the measuring endoscope according to the present invention which utilizes the optical-path difference produced by the birefringence of the polarization-maintaining fiber.

Assuming that the refractive index difference in the polarization-maintaining fiber 18 $(n_x - n_y) = 3*10^{-4}$, wavelength $\lambda = 0.78$ $\mu$m and fiber length $L = 50$ m in the above-mentioned formula (7), the required length of wavelength shift is determined as $\Delta\lambda = 40$ pm. This value is on the order which prevents occurrence of mode hopping even when a semiconductor laser is used as the light source.

Figure 24:
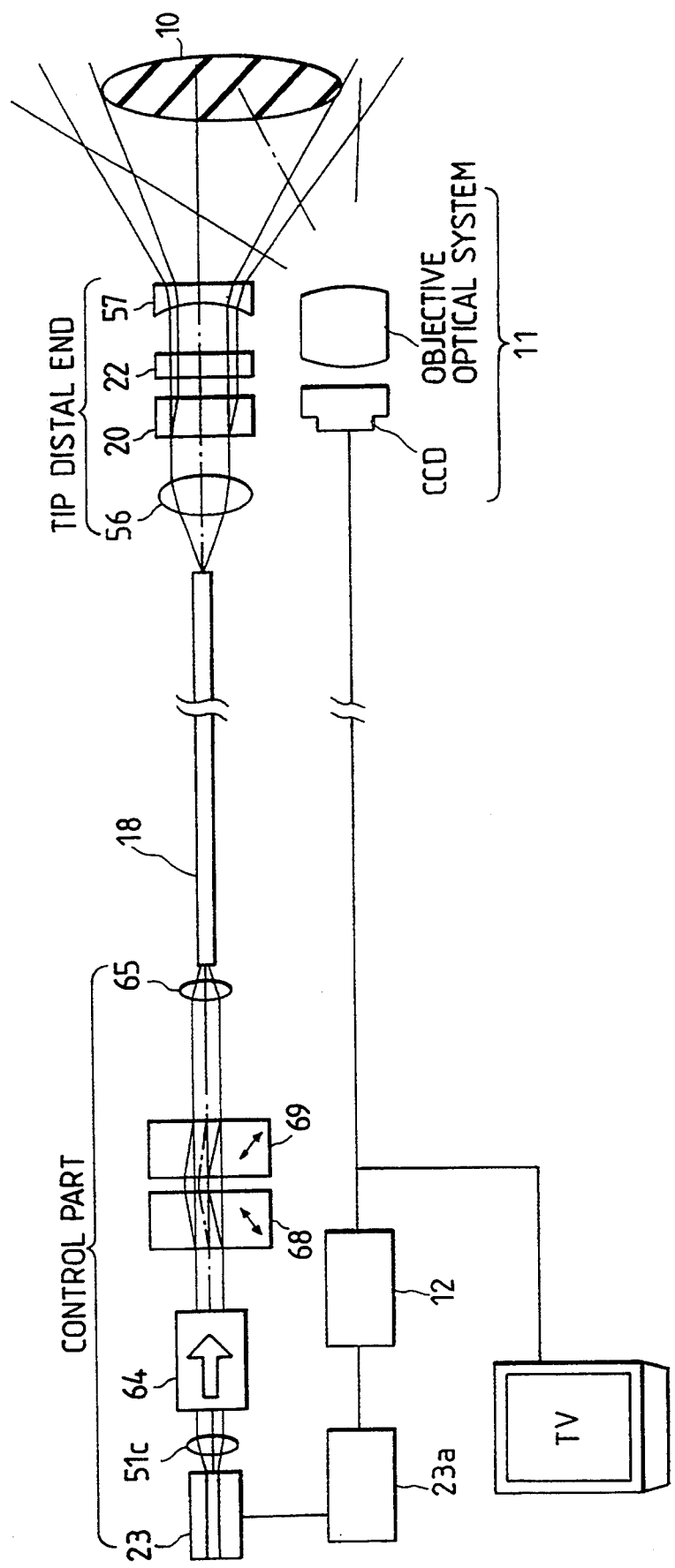
FIG. 24 through FIG. 26 are schematic diagrams illustrating configurations of Embodiments 7 through 9 of the measuring endoscope according to the present invention.

FIG. 24 is a schematic diagram descriptive of Embodiment 7 of the present invention. Different from Embodiment 6 described above, Embodiment 7 is adapted in such a manner that the optical-path difference between the two polarized components perpendicular to each other is produced by two birefringent elements 68, 69 which are interposed in the optical paths. Though the optical-path difference is produced in Embodiment 7 which uses the polarization-maintaining fiber 53, it is possible to control the phase difference to an optimum level with the birefringent elements 68, 69 when the length of the polarization maintaining fiber is limited due to specifications for the measuring endoscope. Embodiment 7 has the configuration and functions which are the similar to those of Embodiment 6. Therefore, the component members of Embodiment 7 which are the same as those of Embodiment 6 will be represented by the same reference numerals and not described particularly.

Figure 25:
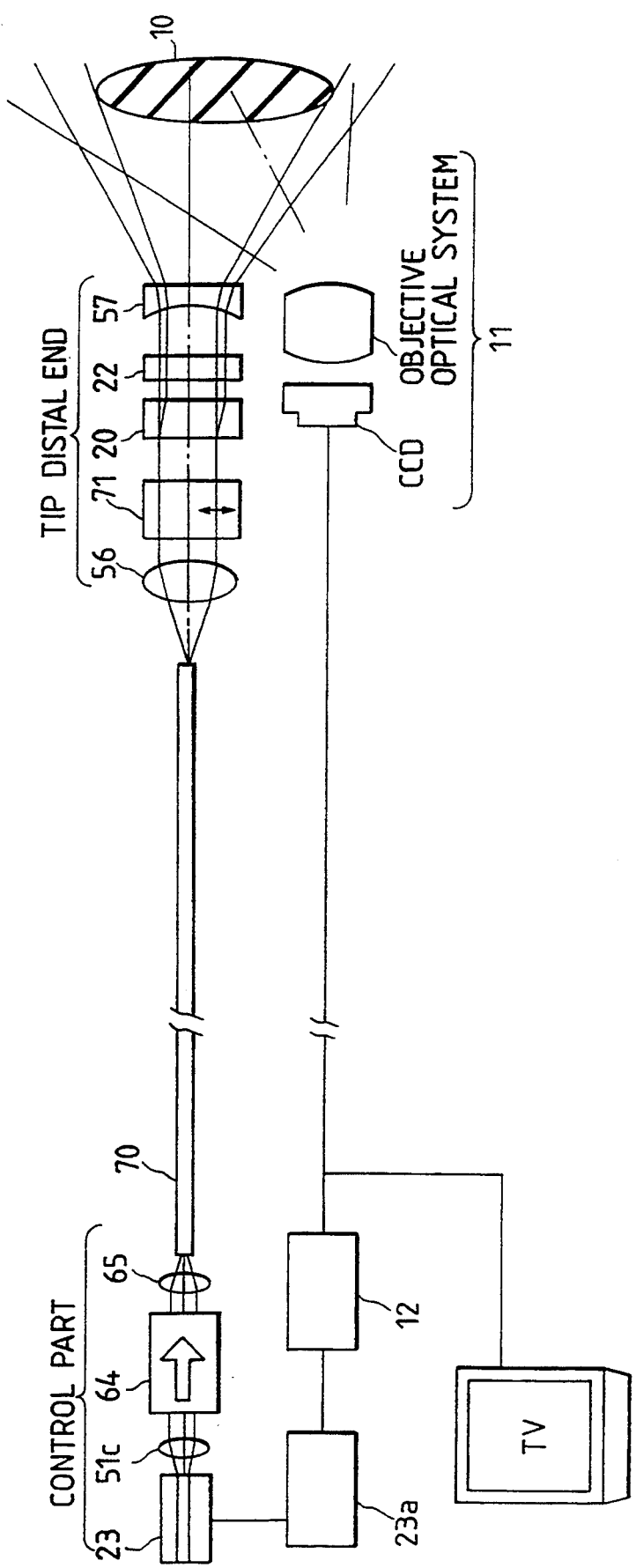

FIG. 25 shows a schematic diagram descriptive of Embodiment 8 of the present invention. Different from Embodiment 7, Embodiment 8 does not comprise the birefringent elements 68 and 69, uses an optical fiber 70 in place of the polarization-maintaining fiber 18 and adopts a phase plate 71 which is interposed between the collimator lens 56 and the birefringent plate 20. In Embodiment 8, the distance of wavelength shift is shortened by reserving a sufficient optical-path length difference in the birefringent plate 20. Accordingly, the two beams which are to interfere with each other travel along optical paths nearly coincident with each other and are scarcely influenced due to external disturbances.

Embodiment 8 has the configuration and function similar to those of Embodiment 6. Therefore, the component members of Embodiment 8, which are the same as those of Embodiment 6, are represented by the same reference numerals and not described particularly. In addition, in Embodiment 8 wherein the optical-path difference is produced in the birefringent plate 18 proper which splits the light beam, the phase plate 71 may be omitted depending on the required distance of wavelength shift.

Figure 26:
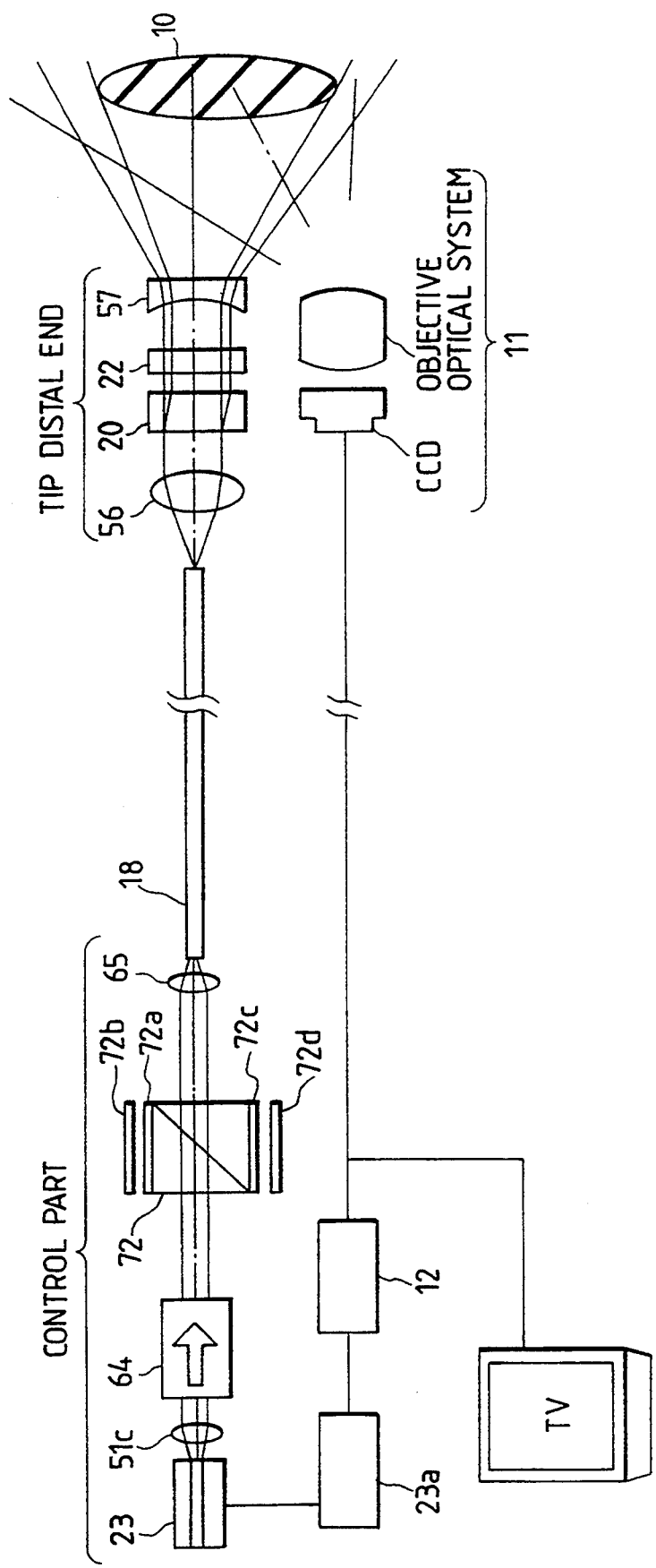

FIG. 26 is a schematic diagram descriptive of Embodiment 9 of the present invention. Different from Embodiment 7, Embodiment 9 is adapted in such a manner that the optical-path difference is produced by a polarizing beam splitter 72 which is adopted in place of the birefringent plates 68, 69. In Embodiment 9, the light beam emitted from the semiconductor laser 51a used as the wavelength variable light source is incident on the polarizing beam splitter 72, and split into two polarized beams which are to be transmitted and reflected respectively. The reflected polarized beam passes through a quarter wave plate 72a, is reflected by a mirror 72b, is transmitted again through the quarter wave plate 72a and falls on the polarizing beam splitter 72. After transmission twice through the quarter wave plate 72a, this polarized beam has a plane of polarization rotated 90°. Therefore, this polarized beam is transmitted through the polarizing beam splitter 72. Then, the polarized beam passes through a quarter wave plate 72c, is reflected by a mirror 72d, is transmitted again through the quarter wave plate 72c and falls on the polarizing beam splitter 72, where after the polarized light beam is reflected by the polarizing beam splitter 72 and travels toward the coupler lens 65. Accordingly, the optical path length is different between the polarized beam which has initially been allowed to traverse the polarizing beam splitter 72 and the polarized beam which has been reflected by the polarizing beam splitter 72. These polarized beams travel through the polarization-maintaining fiber 18 and are separated from each other by the birefringent plate 20 so as to form interference fringes. Embodiment 9 permits changing the distance of wavelength shift by displacing the mirrors 72b, 72d. In addition, the component members of Embodiment 9 which are substantially the same as those used in the preceding embodiments are represented by the same reference numerals.

In each of the embodiments described above, the polarization maintaining fiber may be replaced with an optical fiber which has a certain degree of polarizing property. Further, the electrostrictive strain element, the wavelength changing device for the light source, and the phase changing element compose an interference fringe scanning means.

This invention has been described in relation to what is presently considered to be the most practical and preferred embodiments. However, this application is not intended to be limited to the disclosed embodiments only, but rather is intended to cover all modifications and improvements covered by the spirit and scope of the appended claims.

What is claimed is:

1. A measuring endoscope including an endoscope, said endoscope comprising:
    an illumination optical path having:
        an illumination light source provided as a light source for illuminating an object,
        illumination light transmitting means composed of a plurality of optical fibers whose longitudinal directions coincide with one another, for transmitting light from said illumination light source, and
        a plane of emergence for irradiating said object with the light from said illumination light transmitting means;
    an observation optical path having:
        an objective lens for forming an image of said object with the light reflected from said object,
        image transmitting means provided substantially parallel to said illumination light transmitting means, for transmitting said object image, and
        observing means for observing said object image transmitted by said image transmitting means;
    a tip distal end including:
        the plane of emergence of said illumination optical path, and
        the objective lens of said observation optical path;
    an insertable part whose one end is connected with said tip distal end, extending lengthwise in a longitudinal direction along said illumination light transmitting means and said image transmitting means to be inserted in a narrow space, said insertable part including:
        said illumination light transmitting means of said illumination optical path, and
        said image transmitting means of said observation optical path; and
    a control part connected with the other end of said insertable part, for controlling said tip distal end and said insertable part,
    wherein said measuring endoscope comprises:
        a laser radiation source;
        phase difference changing means connected one of inside said control part and with said control part so that an optical path length of one polarized component in at least one direction, of light emitted from said laser radiation source, is changed with respect to the optical path length of the other polarized component in the other direction perpendicular to the direction of said one polarized component, and thereby a phase difference between two polarized components perpendicular to each other is changed with respect to time;
        a single optical fiber provided substantially parallel to said illumination light transmitting means and said image transmitting means in said insertable part of said endoscope, for transmitting beams of light with the phase difference caused by said phase difference changing means to said tip distal end of said endoscope;
        interference fringe producing means provided in said tip distal end of said endoscope, for producing interference fringes on a surface of said object from the light with the phase difference between said two polarized components perpendicular to each other which are transmitted by said single optical fiber; and
        processing means for calculating a profile of the surface of said object from an image of the interference fringes produced on the surface of said object which are transmitted, together with said object image, by said image transmitting means of said observation optical path;
    wherein the phase difference is changed with respect to time by said phase difference changing means and thereby the interference fringes are scanned.

2. A measuring endoscope including an endoscope, said endoscope comprising:
    an illumination optical path having:
        an illumination light source provided as a light source for illuminating an object,
        illumination light transmitting means composed of a plurality of optical fibers whose longitudinal directions coincide with one an other, for transmitting light from said illumination light source, and
        a plane of emergence for irradiating said object with the light from said illumination light transmitting means;
    an observation optical path having:

an objective lens for forming an image of said object with the light reflected from said object,
image transmitting means provided substantially parallel to said illumination light transmitting means, for transmitting said object image, and
observing means for observing said object image transmitted by said image transmitting means;
a tip distal end including:
the plane of emergence of said illumination optical path, and
the objective lens of said observation optical path;
an insertable part whose one end is connected with said tip distal end, extending lengthwise in a longitudinal direction along said illumination light transmitting means and said image transmitting means to be inserted in a narrow space, said insertable part including:
said illumination light transmitting means of said illumination optical path, and
said image transmitting means of said observation optical path; and
a control part connected with the other end of said insertable part, for controlling said tip distal end and said insertable part,
wherein said measuring endoscope comprises:
a laser radiation source;
polarization state changing means connected one of inside said control part and with said control part, for changing a polarization state of beam of light emitted from said laser radiation source;
a single optical fiber provided substantially parallel to said illumination light transmitting means and said image transmitting means in said insertable part of said endoscope, for transmitting the light beam changed with respect to time of the polarization state by said polarization state changing means to said tip distal end of said endoscope;
interference fringe producing means provided in said tip distal end of said endoscope, for producing interference fringes on a surface of said endoscope, for producing interference fringes on a surface of said object from the light changed with respect to time of the polarization state which is transmitted by said single optical fiber; and
processing means for calculating a profile of the surface of said object from an image of the interference fringes produced on the surface of said object and which are transmitted, together with said object image, by said image transmitting means of said observation optical path,
wherein the polarization state is changed with respect to time by said polarization state changing means and thereby the interference fringes are scanned.

3. A measuring endoscope including an endoscope, said endoscope comprising:
an illumination optical path having:
an illumination light source provided as a light source for illuminating an object,
illumination light transmitting means composed of a plurality of optical fibers whose longitudinal directions coincide with one another, for transmitting light from said illumination light source, and
a plane of emergence for irradiating said object with the light from said illumination light transmitting means;

an observation optical path having:
an objective lens for forming an image of said object with the light reflected from said object,
image transmitting means provided substantially parallel to said illumination light transmitting means, for transmitting said object image, and
observing means for observing said object image transmitted by said image transmitting means;
a tip distal end including:
the plane of emergence of said illumination optical path, and
the objective lens of said observation optical path;
an insertable part whose one end is connected with said tip distal end, extending lengthwise in a longitudinal direction along said illumination light transmitting means and said image transmitting means to be inserted in a narrow space, said insertable part including:
said illumination light transmitting means of said illumination optical path, and
said image transmitting means of said observation optical path; and
a control part connected with the other end of said insertable part, for controlling said tip distal end and said insertable part,
wherein said measuring endoscope comprises:
a laser radiation source;
wavelength selective means connected inside said control part or with said control part, for changing a wavelength of a beam of light, with respect to time, emitted from said laser radiation source;
a single optical fiber provided substantially parallel to said illumination light transmitting means and said image transmitting means in said insertable part of said endoscope, for transmitting the light beam changed in wavelength by said wavelength selective means to said tip distal end of said endoscope;
interference fringe producing means provided in said tip distal end of said endoscope, for producing interference fringes on a surface of said object from the light whose wavelength is changed with respect to time which is transmitted by said single optical fiber; and
processing means for calculating a profile of the surface of said object from an image of the interference fringes produced on the surface of said object which are transmitted, together with said object image, by said image transmitting means of said observation optical path,
wherein the wavelength is changed with respect to time by said wavelength selective means and thereby the interference fringes are scanned.

4. A measuring endoscope according to claim 2, wherein said interference fringe producing means includes at least a beam splitter for splitting a beam of light into two components, said beam splitter providing coherent light with an optical path difference and having two mirrors making an arbitrary angle for producing the interference fringes.

5. A measuring endoscope according to claim 3, wherein said interference fringe producing means includes at least a beam splitter for splitting a beam of light into two components, said beam splitter providing coherent light with an optical path difference and having two mirrors making an arbitrary angle for producing the interference fringes.

6. A measuring endoscope according to claim 1, wherein said interference fringe producing means has a polarizer for splitting light into polarized components in difference directions of vibrations and an analyzer for causing the directions of vibrations of the polarized components to coincide with each other.

7. A measuring endoscope according to claim 2, wherein said interference fringe producing means has a polarizer for splitting light into polarized components in difference directions of vibrations and an analyzer for causing the directions of vibrations of the polarized components to coincide with each other.

8. A measuring endoscope according to claim 3, wherein said interference fringe producing means has a polarizer for splitting light into polarized Components in difference directions of vibrations and an analyzer for causing the directions of vibrations of the polarized components to coincide with each other.

* * * * *